(12) United States Patent
Rajagopal et al.

(10) Patent No.: US 9,382,570 B2
(45) Date of Patent: Jul. 5, 2016

(54) LIVE BIOLOAD DETECTION USING MICROPARTICLES

(71) Applicant: 3M INNOVATIVE PROPERTIES COMPANY, St. Paul, MN (US)

(72) Inventors: Raj Rajagopal, Woodbury, MN (US); Kurt J. Halverson, Lake Elmo, MN (US); Manjiri T. Kshirsagar, Woodbury, MN (US); James E. Aysta, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 27 days.

(21) Appl. No.: 14/069,416

(22) Filed: Nov. 1, 2013

(65) Prior Publication Data

US 2014/0057341 A1  Feb. 27, 2014

Related U.S. Application Data

(62) Division of application No. 13/142,290, filed as application No. PCT/US2009/069898 on Dec. 31, 2009, now Pat. No. 8,609,330.

(60) Provisional application No. 61/141,685, filed on Dec. 31, 2008, provisional application No. 61/291,301, filed on Dec. 30, 2009.

(51) Int. Cl.

| | |
|---|---|
| *C12M 1/34* | (2006.01) |
| *C12M 3/00* | (2006.01) |
| *C12M 1/00* | (2006.01) |
| *C12Q 1/68* | (2006.01) |
| *G01N 15/06* | (2006.01) |
| *G01N 33/00* | (2006.01) |
| *G01N 33/48* | (2006.01) |
| *C12Q 1/04* | (2006.01) |
| *B01L 3/00* | (2006.01) |
| *C12M 1/24* | (2006.01) |
| *C12M 1/30* | (2006.01) |
| *G01N 33/569* | (2006.01) |
| *A61B 10/00* | (2006.01) |
| *A61B 10/02* | (2006.01) |

(52) U.S. Cl.
CPC ............... *C12Q 1/04* (2013.01); *B01L 3/5082* (2013.01); *C12M 23/08* (2013.01); *C12M 23/32* (2013.01); *C12M 23/34* (2013.01); *C12M 33/02* (2013.01); *G01N 33/56916* (2013.01); *A61B 10/0045* (2013.01); *A61B 10/02* (2013.01); *B01L 2200/026* (2013.01); *B01L 2200/10* (2013.01); *G01N 2333/245* (2013.01)

(58) Field of Classification Search
None
See application file for complete search history.

(56) References Cited

U.S. PATENT DOCUMENTS

| | | | |
|---|---|---|---|
| 3,481,712 | A | 12/1969 | Bernstein et al. |
| 3,745,090 | A | 7/1973 | Chappelle et al. |
| 3,897,902 | A | 8/1975 | Yanez, Jr. |
| 3,933,592 | A | 1/1976 | Clendenning |
| 3,971,703 | A | 7/1976 | Picciolo et al. |
| 4,144,134 | A | 3/1979 | Plakas |
| 4,184,483 | A | 1/1980 | Greenspan |
| 4,303,752 | A | 12/1981 | Kolehmainen et al. |
| 4,421,848 | A | 12/1983 | Whitlock |
| 4,503,149 | A | 3/1985 | Boyd |
| 4,698,311 | A | 10/1987 | Hall et al. |
| 4,729,846 | A | 3/1988 | Matsui et al. |
| 4,906,565 | A | 3/1990 | Vossen |
| 4,978,504 | A | 12/1990 | Nason |
| 5,238,812 | A | 8/1993 | Coulter et al. |
| 5,258,285 | A | 11/1993 | Aegidius |
| 5,264,184 | A | 11/1993 | Aysta et al. |
| 5,576,185 | A | 11/1996 | Coulter et al. |
| 5,595,653 | A | 1/1997 | Good et al. |
| 5,695,989 | A | 12/1997 | Kalamasz |
| 5,827,675 | A | 10/1998 | Skiffington et al. |
| 5,891,702 | A | 4/1999 | Sakakibara et al. |
| 5,905,029 | A | 5/1999 | Andreotti et al. |
| 5,908,751 | A | 6/1999 | Higo et al. |
| 5,965,453 | A * | 10/1999 | Skiffington ............. B01L 3/502 422/52 |
| 6,045,913 | A | 4/2000 | Castle |
| 6,140,040 | A | 10/2000 | Palm et al. |
| 6,174,704 | B1 | 1/2001 | Chu et al. |
| 6,200,767 | B1 | 3/2001 | Sakakibara et al. |
| 6,451,260 | B1 | 9/2002 | Düsterhöft et al. |
| 6,465,201 | B1 | 10/2002 | Presente et al. |
| 6,588,681 | B2 | 7/2003 | Rothrum et al. |
| 6,660,489 | B2 | 12/2003 | Schrecengost et al. |
| 6,699,987 | B2 | 3/2004 | Hillebrand et al. |
| 6,824,560 | B2 | 11/2004 | Pelton |

(Continued)

FOREIGN PATENT DOCUMENTS

| | | |
|---|---|---|
| DE | 1 442 223 | 11/1969 |
| EP | 1 661 988 | 5/2006 |

(Continued)

OTHER PUBLICATIONS

Stratagene Catalog (1988), p. 39. Published by Stratgene, 11011 North Torrey Pines Road, La Jolla, CA 92037, USA.*
"ATP test" from Wikipedia, the free encyclopedia. Printed on Feb. 25, 2013.
Berry, E.D. et al.; "Hydroxyapatite Adherence as a Means to Concentrate Bacteria"; Applied and Environmental Microbiology; vol. 63, No. 10; 1997; pp. 4069-4074.
Cho, M. et al.; "A Bioluminescent Cytotoxicity Assay for Assessment of Membrane Integrity Using a Proteolytic Biomarker"; Toxicol. In Vitro; vol. 22, No. 4; 2008; pp. 1099-1106.
(Continued)

*Primary Examiner* — Frank Lu
(74) *Attorney, Agent, or Firm* — Qiang Han

(57) ABSTRACT

The present invention provides methods to concentrate cells onto microparticles, to concentrate the microparticles, and to detect the cells. The present invention also includes unitary sample preparation and detection devices to be used in accordance with the methods.

19 Claims, 16 Drawing Sheets

(56) References Cited

U.S. PATENT DOCUMENTS

| | | | |
|---|---|---|---|
| 6,861,067 B2 | 3/2005 | McGhee et al. | |
| 6,967,261 B1 | 11/2005 | Soerens et al. | |
| 7,005,143 B2 | 2/2006 | Abuelyaman et al. | |
| 7,045,913 B2 | 5/2006 | Ebrahim et al. | |
| 7,083,911 B2 | 8/2006 | Wood et al. | |
| 7,141,033 B2 | 11/2006 | Kanjilal et al. | |
| 7,282,181 B2 | 10/2007 | Hudak et al. | |
| 7,338,692 B2 | 3/2008 | Smith et al. | |
| 7,422,868 B2 | 9/2008 | Fan et al. | |
| 7,485,609 B2 | 2/2009 | Reddy et al. | |
| 7,553,417 B2 | 6/2009 | Waller, Jr. et al. | |
| 7,824,732 B2 | 11/2010 | Sahouani et al. | |
| 2003/0104507 A1 | 6/2003 | Wood et al. | |
| 2004/0124085 A1 | 7/2004 | Tai et al. | |
| 2004/0157971 A1 | 8/2004 | Kim | |
| 2004/0161788 A1 | 8/2004 | Chen et al. | |
| 2004/0197845 A1 | 10/2004 | Hassibi et al. | |
| 2005/0048592 A1 | 3/2005 | Wood et al. | |
| 2005/0070701 A1 | 3/2005 | Hochstetler et al. | |
| 2005/0142571 A1 | 6/2005 | Parthasarathy et al. | |
| 2005/0152992 A1 | 7/2005 | Johnson, Jr. et al. | |
| 2005/0153423 A1 | 7/2005 | Baba et al. | |
| 2005/0181467 A1 | 8/2005 | Schrecengost et al. | |
| 2005/0250138 A1 | 11/2005 | Young et al. | |
| 2005/0272111 A1 | 12/2005 | Bryan et al. | |
| 2006/0062854 A1 | 3/2006 | Chandra et al. | |
| 2006/0166347 A1 | 7/2006 | Faulstich et al. | |
| 2006/0273049 A1 | 12/2006 | Leach et al. | |
| 2007/0148458 A1 | 6/2007 | Sahouani et al. | |
| 2007/0212266 A1 | 9/2007 | Johnston et al. | |
| 2007/0269341 A1 | 11/2007 | Halverson et al. | |
| 2008/0023408 A1 | 1/2008 | Hansen | |
| 2008/0064939 A1 | 3/2008 | Reynolds et al. | |
| 2008/0153125 A1 | 6/2008 | Buttry et al. | |
| 2008/0207794 A1 | 8/2008 | Wright et al. | |
| 2009/0068065 A1 | 3/2009 | Pagoria et al. | |
| 2010/0190171 A1 | 7/2010 | Kshirsagar et al. | |
| 2010/0209927 A1 | 8/2010 | Menon et al. | |
| 2010/0209961 A1 | 8/2010 | Kshirsagar et al. | |
| 2010/0248214 A1 | 9/2010 | Kshirsagar et al. | |

FOREIGN PATENT DOCUMENTS

| | | |
|---|---|---|
| EP | 1 845 375 | 10/2007 |
| GB | 2 138 021 | 10/1984 |
| GB | 2 433 219 | 6/2007 |
| JP | 06-245795 | 9/1994 |
| JP | 11-028099 | 2/1999 |
| JP | H11-514849 | 12/1999 |
| JP | 2005-012518 | 2/2005 |
| JP | 2005-098022 | 10/2005 |
| WO | WO 89/09279 | 10/1989 |
| WO | WO 96/07759 | 3/1996 |
| WO | WO 96/14570 | 5/1996 |
| WO | WO 97/02812 | 1/1997 |
| WO | WO 97/03209 | 1/1997 |
| WO | WO 00/29112 | 5/2000 |
| WO | WO 2005/045075 | 5/2005 |
| WO | WO 2005/071388 | 8/2005 |
| WO | WO 2005/094792 | 10/2005 |
| WO | WO 2007/113583 | 10/2007 |
| WO | WO 2007/137257 | 11/2007 |
| WO | WO 2007/146722 | 12/2007 |
| WO | WO 2008/075044 | 6/2008 |
| WO | WO 2008/122908 | 10/2008 |
| WO | WO 2008/129517 | 10/2008 |
| WO | WO 2008/134472 | 11/2008 |
| WO | WO 2008/150779 | 12/2008 |
| WO | WO 2009/009188 | 1/2009 |
| WO | WO 2009/046081 | 4/2009 |
| WO | WO 2009/046183 | 4/2009 |
| WO | WO 2009/046191 | 4/2009 |
| WO | WO 2009/048743 | 4/2009 |
| WO | WO 2009/061864 | 5/2009 |
| WO | WO 2009/067498 | 5/2009 |
| WO | WO 2009/067503 | 5/2009 |
| WO | WO 2009/067513 | 5/2009 |
| WO | WO 2009/067518 | 5/2009 |
| WO | WO 2009/076267 | 6/2009 |
| WO | WO 2009/082667 | 7/2009 |
| WO | WO 2009/085357 | 7/2009 |
| WO | WO 2009/102859 | 8/2009 |
| WO | WO 2009/137138 | 11/2009 |
| WO | WO 2009/140356 | 11/2009 |
| WO | WO 2010/039627 | 4/2010 |
| WO | WO 2010/078399 | 7/2010 |
| WO | WO 2010/078404 | 7/2010 |
| WO | WO 2010/129726 | 11/2010 |
| WO | WO 2010/129727 | 11/2010 |
| WO | WO 2010/129728 | 11/2010 |
| WO | WO 2011/079038 | 6/2011 |
| WO | WO 2011/082309 | 7/2011 |

OTHER PUBLICATIONS

Crouch, S.P.M. et al.; "The use of ATP bioluminescence as a measure of cell proliferation and cytotoxicity"; Journal of Immunological Methods; vol. 160; 1993; pp. 81-88.

DeLuca, M. et al.; "Factors Affecting the Kinetics of Light Emission from Crude and Purified Firefly Luciferase"; Analytical Biochemistry; vol. 95; 1979; pp. 194-198.

Gorus, F. et al.; "Applications of Bio- and Chemiluminescence in the Clinical Laboratory"; Clinical Chemistry; vol. 25, No. 4; 1979; pp. 512-519.

Harvey, E.N. "A History of Luminescence—From the Earliest Times Until 1900"; American Philosophical Society, Philadelphia, PA 1957 (cover, copyright, and Table of Contents consisting of 12 pgs).

Lee JiYoung et al.; "Detection of *E. coli* in beach water within 1 hour using immunomagnetic separation and ATP bioluminescence"; Luminescence; vol. 19, No. 1; 2004; pp. 31-36.

McElroy, W.D. et al.; "Factors Influencing the Response of the Bioluminescent Reaction to Adenosine Triphosphate"; Archives of Biochemistry; vol. 22; 1949; pp. 420-433.

Morbe, J.L. et al.; "Release of miniantibodies from *E. coli* cells into the supernatant at low and high cell densities": Micorbiol. Res.; vol. 152; No. 4; 1997; pp. 385-394.

Navrátil, M. et al.; "Chapter 34—Bioluminescence in Immobilized Cells for Biomass Detection and Biosensor Applications"; Methods in Biotechnology: Immobilization of Enzymes and Cells, Second Edition; vol. 22; 2006; pp. 393-401.

Oster, J., et al.; "Polyvinyl-alcohol-based magnetic beads for rapid and efficient separation of specific or unspecific nucleic acid sequences"; Journal of Magnetism and Magnetic Materials; vol. 225; 2001; pp. 145-150.

Stanley, P.E.; "[2] Extraction of Adenosine Triphosphate from Microbial and Somatic Cells"; Methods in Enzymology; vol. 133; Bioluminescence and Chemiluminescence Part B; 1986; pp. 14-22.

Abstract entitled "Waterborne Cryptosporidium parvum detection using the particle filtration system and quantitative PCR"; from General Meeting of the American Society for Microbiology; vol. 103; 2003; p. Q-096.

Abstract entitled "Use of fluorescent microspheres to evaluate the particle filtration system for waterborne pathogen detection"; from General Meeting of the American Society for Microbiology; vol. 103; 2003; pp. Q-268.

"Standard Methods for the Examination of Water and Wastewater," $20^{th}$ Edition; Edited by L. S. Clesceri et al.; American Public Health Association; 1998, Title, copyright and Table of Contents 23 pages.

Lee et al., "Microfluidic Immunoassay Platform Using Antibody-immobilized Glass Beads and Its Application for Detection of *Escherichia coli* O157:H7", Bull. Korean Chem. Soc. 2006, vol. 27, No. 4, pp. 479-483.

\* cited by examiner

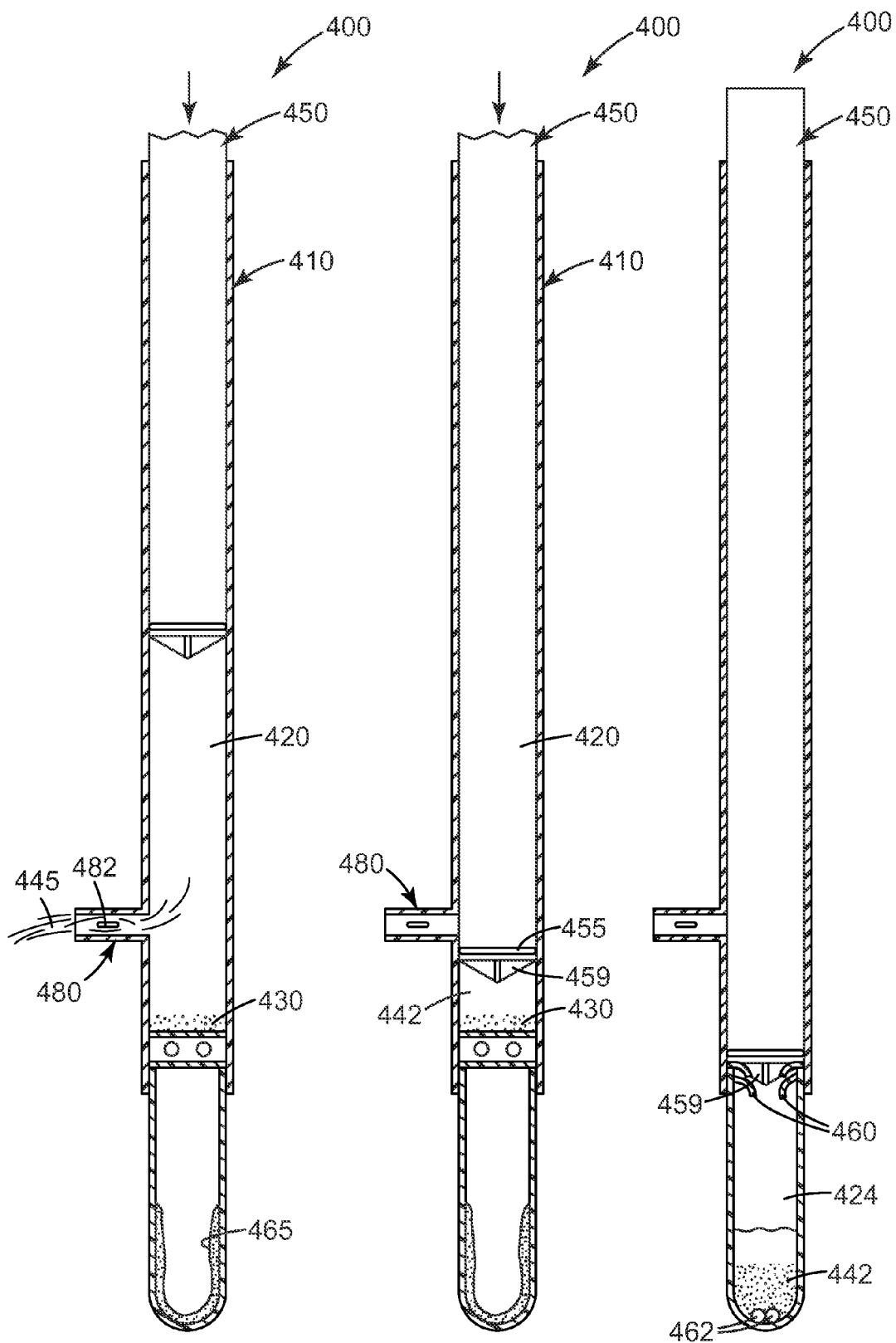
*Fig. 4B*  *Fig. 4C*  *Fig. 4D*

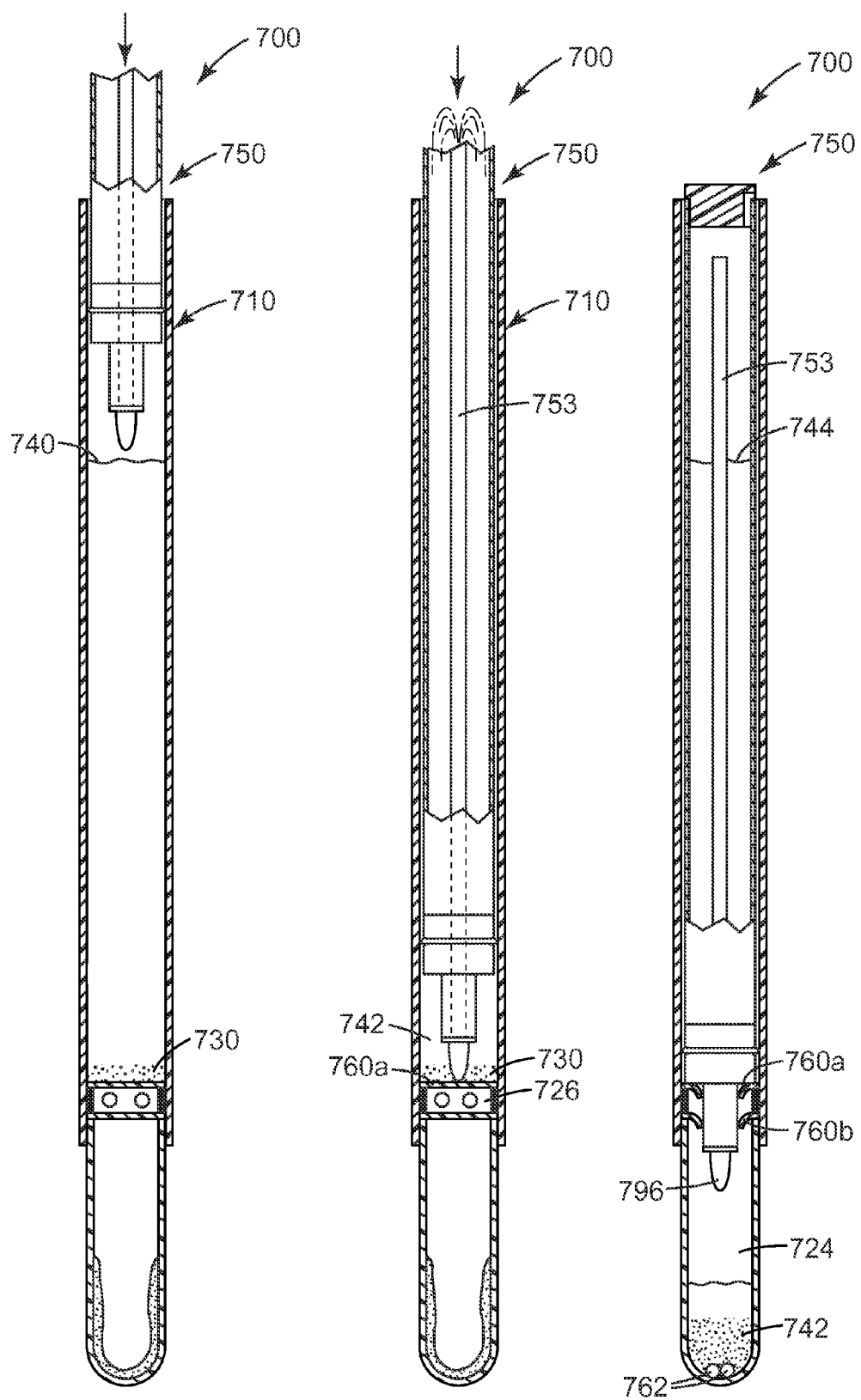

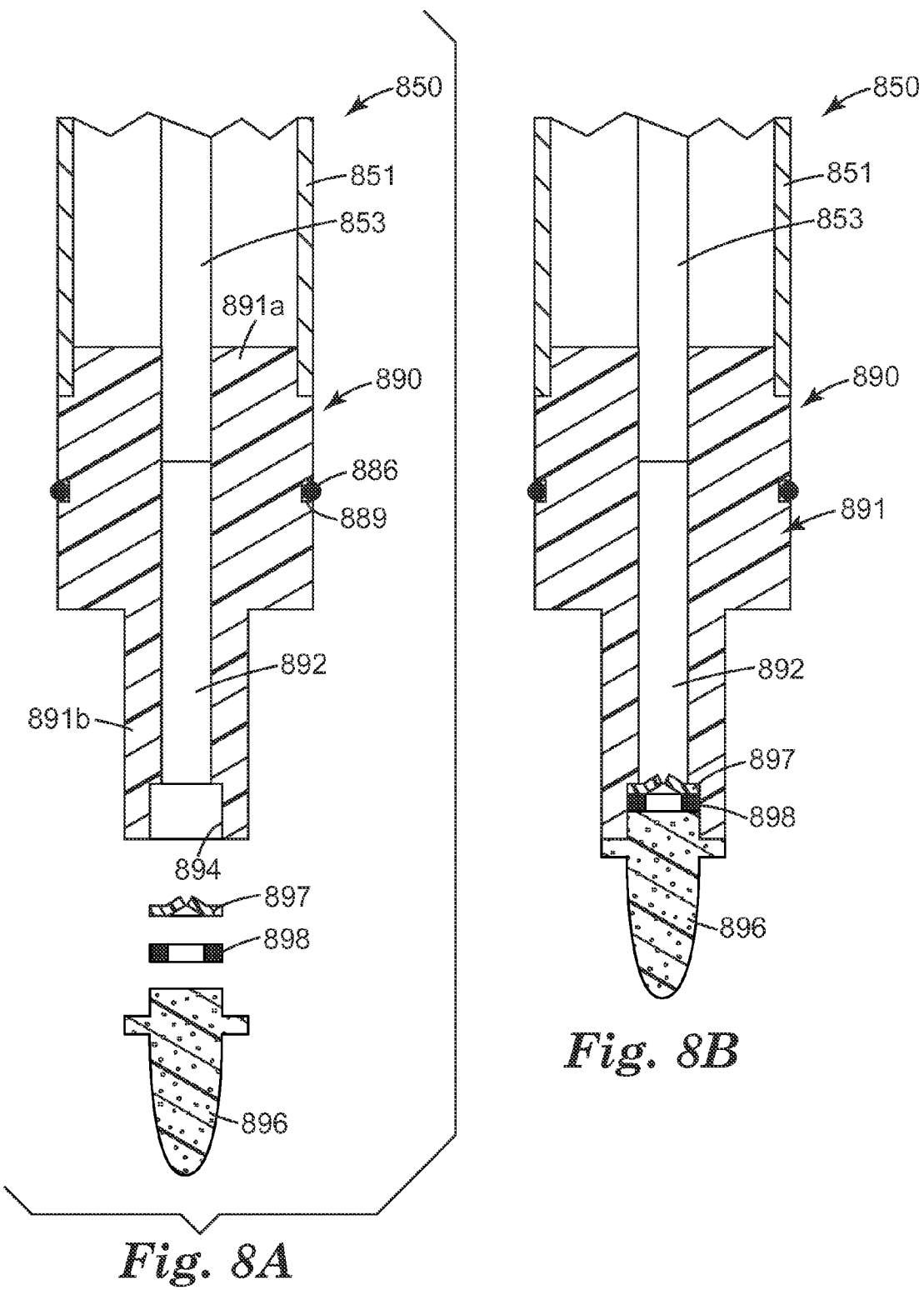

LIVE BIOLOAD DETECTION USING MICROPARTICLES

CROSS REFERENCE TO RELATED APPLICATIONS

This application is a division of U.S. patent application Ser. No. 13/142,290, U.S. Pat. No. 8,609,330 B2, filed Sep. 21, 2011, which application is a national stage filing under 35 U.S.C. 371 of PCT/US2009/069898, filed Dec. 31, 2009, which claims the benefit of U.S. Provisional Patent Application No. 61/141,685, filed Dec. 31, 2008 and U.S. Provisional Patent Application No. 61/291,301, filed Dec. 30, 2009, which are incorporated herein by reference.

BACKGROUND

Various tests are available that can be used to assess the presence of biological analytes in a sample (e.g. surface, water, air, etc). Such tests include those based on the detection of ATP using the firefly luciferase reaction, tests based on the detection of protein using colorimetry, tests based on the detection of microorganisms using microbiological culture techniques, and tests based on detection of microorganisms using immunochemical techniques. Surfaces can be sampled using either a swab device or by direct contact with a culture device such as an agar plate. The sample can be analyzed for the presence of live cells and, in particular, live microorganisms.

Results from these tests are often used to make decisions about the cleanliness of a surface. For example, the test may be used to decide whether food-processing equipment has been cleaned well enough to use for production. Although the above tests are useful in the detection of a contaminated surface, they can require numerous steps to perform the test, they may not be able to distinguish quickly and/or easily the presence of live cells from dead cells and, in some cases, they can require long periods of time (e.g., hours or days) before the results can be determined.

The tests may be used to indicate the presence of live microorganisms. For such tests, a cell extractant is often used to release a biological analyte (e.g., ATP) associated with living cells. The presence of extracellular material (e.g., non-cellular ATP released into the environment from dead or stressed animal cells, plant cells, and/or microorganisms) can create a high "background" level of ATP that can complicate the detection of live cells.

In spite of the availability of a number of methods and devices to detect live cells, there remains a need for a simple, reliable test for detecting live cells and, in particular, live microbial cells.

SUMMARY OF THE INVENTION

In general, the present disclosure relates to articles and methods for detecting live cells in a sample. The articles and methods make possible the rapid detection (e.g., through fluorescence, chemiluminescence, or a color reaction) of the presence of cells such as bacteria on a surface. In some embodiments, the inventive articles are "sample-ready", i.e., the articles contain all of the necessary features to detect living cells in a sample. In some aspects, the inventive articles and methods provide a means to distinguish a biological analyte, such as ATP or an enzyme, that is associated with eukaryotic cells (e.g., plant or animal cells) from a similar or identical biological analyte associated with prokaryotic cells (e.g., bacterial cells). Furthermore, the inventive articles and methods provide a means to distinguish a biological analyte that is free in the environment (i.e., an acellular biological analyte) from a similar or identical biological analyte associated with a living cell.

Methods of the present disclosure allow an operator to concentrate cells from a liquid sample and to detect an analyte associated with the cells. In certain embodiments, detection of the analyte may be an indicator of live cells including, in particular, live microbial cells in the sample. In some embodiments, the methods provide for the operator to measure the amount of a biological analyte in the sample. In some embodiments, the methods provide for the operator to, after a predetermined period of time during which an effective amount of a cell extractant is released from a composition into the liquid mixture, measure the amount of a biological analyte to determine differentially the amount of biological analyte from acellular material and from live cells in the sample. In some embodiments, the methods provide for the operator, within a first predetermined period of time, to perform a first measurement of the amount of a biological analyte and, within a second predetermined period of time during which an effective amount of cell extractant is released from the composition, perform a second measurement of the amount of biological analyte to detect the presence of live cells in the sample. In some embodiments, the methods can allow the operator to distinguish whether biological analyte in the sample was released from live plant or animal cells or whether it was released from live microbial cells (e.g., bacteria). The present invention is capable of use by operators under the relatively harsh field environment of institutional food preparation services, health care environments and the like.

In one aspect, the present disclosure provides a method of detecting cells in a sample. The method comprises providing a cell concentration agent, a hydrogel comprising a cell extractant and a liquid sample suspected of containing cells. The method further comprises contacting the liquid sample and the cell concentration agent for a period of time, isolating the cell concentration agent from at least a portion of the liquid sample, forming a liquid mixture comprising the isolated cell concentration agent and the hydrogel wherein the cell extractant is released into the mixture, and detecting a biological analyte. Optionally, the analyte can be detected at two or more discrete time points. In some embodiments, detecting a biological analyte comprises detecting a live cell. In some embodiments, detecting a biological analyte comprises using a detection system. In some embodiments, detecting a biological analyte comprises quantifying the analyte. In some embodiments, detecting a biological analyte comprises detecting ATP from a cell. In some embodiments, detecting a biological analyte comprises detecting the cell by genetic or immunological methods. In some embodiments, the method further comprises the steps of providing a somatic cell extractant and contacting the somatic cell extractant with cells from the sample.

In another aspect, the present disclosure provides a method of detecting cells in a sample. The method comprises providing a sample suspected of containing cells; a cell concentration agent; a hydrogel comprising a cell extractant; a detection article comprising a housing with two or more receptacles and an opening configured to receive the sample; means for isolating and transferring the cell concentration agent from a upper receptacle to a lower receptacle in the housing. The method further comprises contacting in a liquid medium the sample and the cell concentration agent in the upper receptacle of the housing. The method further comprises transferring the cell concentration agent to the lower receptacle in the housing. The method further comprises forming a liquid mixture comprising the isolated cell concentration agent and the hydrogel, wherein the cell extractant is released into the mixture. The method further comprises detecting a biological analyte. Optionally, the biological analyte can be detected at two or more discrete time points. In some embodiments, detecting a biological analyte comprises detecting a live cell. In some embodiments, detecting a biological analyte comprises using a detection system. In some embodiments, detecting a biological analyte comprises quantifying the analyte. In some embodiments, detecting a biological analyte comprises detecting ATP from a cell. In some embodiments, detecting a biological analyte comprises detecting the cell by genetic or immunological methods. In some embodiments, the method further comprises the steps of providing a somatic cell extractant and contacting the somatic cell extractant with cells from the sample.

In another aspect, the present disclosure provides a method of detecting cells in a sample. The method comprises providing a sample suspected of containing cells; a detection article comprising a housing with an opening configured to receive the sample, a upper receptacle containing a cell concentration agent, and a lower receptacle containing a hydrogel comprising a cell extractant; means for isolating the cell concentration agent from at least a portion of the liquid sample; and means for transferring the cell concentration agent from the upper receptacle to the lower receptacle in the housing. The method further comprises contacting in a liquid medium the sample and the cell concentration agent in the upper receptacle of the housing. The method further comprises isolating and transferring the cell concentration agent to the lower receptacle of the housing. The method further comprises forming a liquid mixture comprising the isolated cell concentration agent and the hydrogel, wherein the cell extractant is released into the mixture. The method further comprises detecting a biological analyte. Optionally, the biological analyte can be detected at two or more discrete time points. In some embodiments, detecting a biological analyte comprises detecting a live cell. In some embodiments, detecting a biological analyte comprises using a detection system. In some embodiments, detecting a biological analyte comprises quantifying the analyte. In some embodiments, detecting a biological analyte comprises detecting ATP from a cell. In some embodiments, detecting a biological analyte comprises detecting the cell by genetic or immunological methods. In some embodiments, the method further comprises the steps of providing a somatic cell extractant and contacting the somatic cell extractant with cells from the sample.

In another aspect, the present disclosure provides a unitary sample preparation and detection device. The device comprises a housing comprising at least two receptacles with a passageway therebetween. An upper receptacle of the housing comprises an opening configured to receive a sample and a cell concentration agent disposed therein. A lower receptacle of the housing comprises a detection reagent disposed therein. The device further comprises means for isolating the upper receptacle from the lower receptacle. The device further comprises means for transferring the cell concentration agent from the upper receptacle to the lower receptacle. In some embodiments, the means for isolating the first and lower receptacles is the means for transferring the cell concentration agent from the upper receptacle to the lower receptacle. In some embodiments, the housing further comprises a frangible seal between the two isolated receptacles. In some embodiments, the upper receptacle comprises a taper region. In some embodiments, the device further comprises a hydrogel comprising a cell extractant. In some embodiments, the housing further comprises a third receptacle. In some embodiments, the device further comprises a sample acquisition device. In some embodiments, the detection reagent comprises a reagent for detecting ATP. In some embodiments, the device further comprises a hydrogel comprising a detection reagent.

In another aspect, the present disclosure provides a unitary sample preparation and detection device. The device comprises a housing comprising at least two isolated receptacles with a passageway therebetween and a piston configured to fit the passageway. An upper receptacle in the housing comprises an opening configured to receive a sample and a cell concentration agent disposed therein. A lower receptacle of the housing comprises a detection reagent disposed therein. In some embodiments, the housing further comprises a frangible seal between the two isolated receptacles. In some embodiments, the upper receptacle comprises a tapered inner wall. In some embodiments, the device further comprises a hydrogel comprising a cell extractant. In some embodiments, the housing further comprises a third isolated receptacle. In some embodiments, the device further comprises a sample acquisition device. In some embodiments, the detection reagent comprises a reagent for detecting ATP. In some embodiments, the device further comprises a slow-release composition comprising a detection reagent.

In another aspect, the present disclosure provides a unitary sample preparation and detection device. The device comprises a housing comprising at least two isolated receptacles with a passageway therebetween. An upper receptacle of the housing comprises an opening configured to receive a sample and a cell concentration agent disposed therein. A lower receptacle comprises a detection reagent disposed therein. The device further comprises a valve configured to control the passage of material from the upper receptacle to the lower receptacle. In some embodiments, the upper receptacle comprises a tapered inner wall. In some embodiments, the device further comprises a hydrogel comprising a cell extractant. In some embodiments, the housing further comprises a third isolated receptacle. In some embodiments, the device further comprises a sample acquisition device. In some embodiments, the detection reagent comprises a reagent for detecting ATP. In some embodiments, the device further comprises a slow-release composition comprising a detection reagent.

In another aspect, the present disclosure provides a kit comprising a housing comprising at least two isolated receptacles with a passageway therebetween and means for transferring the cell concentration agent from an upper receptacle to a lower receptacle. The upper receptacle of the housing comprises an opening configured to receive a sample. The lower receptacle comprises a detection reagent disposed therein. The kit further comprises a cell concentration agent. In some embodiments, the cell concentration agent is disposed in the upper receptacle of the housing. In some embodiments, the kit further comprises hydrogel comprising a microbial cell extractant. In some embodiments, the kit further comprises a somatic cell extractant. In some embodiments, the kit further comprises a sample acquisition device.

In another aspect, the present disclosure provides a kit comprising a housing comprising at least two isolated receptacles with a passageway therebetween. An upper receptacle in the housing comprises an opening configured to receive a sample. A lower receptacle in the housing comprises a detection reagent disposed therein. The kit further comprises a cell concentration agent and means for transferring the cell concentration agent from the upper receptacle to the lower receptacle. In some embodiments, the cell concentration agent is disposed in the upper receptacle of the housing. In some embodiments, the kit further comprises hydrogel comprising a microbial cell extractant. In some embodiments, the kit further comprises a somatic cell extractant. In some embodiments, the kit further comprises a sample acquisition device.

GLOSSARY

"Biological analytes", as used herein, refers to molecules, or derivatives thereof, that occur in or are formed by an organism. For example, a biological analyte can include, but is not limited to, at least one of an amino acid, a nucleic acid, a polypeptide, a protein, a nucleotide, a polynucleotide, a lipid, a phospholipid, a saccharide, a polysaccharide, and combinations thereof. Specific examples of biological analytes can include, but are not limited to, a metabolite (e.g., a small molecule, such as ATP, or a polypeptide, such as protein A), an allergen (e.g., peanut allergen(s), a hormone, a toxin (e.g., *Bacillus* diarrheal toxin, aflatoxin, etc.), RNA (e.g., mRNA, total RNA, tRNA, etc.), DNA (e.g., plasmid DNA, plant DNA, etc.), a tagged protein, an antibody, an antigen, and combinations thereof.

"Liquid sample", as used herein, refers to a sample material that comprises a liquid. The sample may, in its original form, comprise a liquid such as, for example, water, milk, juice, blood, wound exudate, and the like. Alternatively, the liquid sample can be a suspension of solids in a liquid suspending medium (e.g., water, an aqueous buffer). For example, a solid, semisolid, or gelatinous sample can be collected with a sample acquisition device and suspended in a liquid to form a liquid sample.

"Clarified liquid sample" refers to the bulk of a liquid sample that remains after the liquid sample has been contacted with a cell concentration agent and the cell concentration agent has been partitioned (e.g., by sedimentation, filtration, centrifugation, or precipitation) from the bulk of the liquid.

"Sample acquisition device" is used herein in the broadest sense and refers to an implement used to collect a liquid, semisolid, or solid sample material. Nonlimiting examples of sample acquisition devices include swabs, wipes, sponges, scoops, spatulas, pipettes, pipette tips, and siphon hoses.

"Dead-end valve", as used herein, refers to a type of valve that is used to regulate the transfer of material (e.g., liquids, solids, or a suspension of solids in a liquid) between two or more receptacles in the housing of a detection device. The dead-end valve is designed such that the cavity in the valve that is used to transfer the material can only be in fluid communication with one of the receptacles at a time.

As used herein, the term "hydrogel" refers to a polymeric material that is hydrophilic and that is either swollen or capable of being swollen with a polar solvent. The polymeric material typically swells but does not dissolve when contacted with the polar solvent. That is, the hydrogel is insoluble in the polar solvent. The swollen hydrogel can be dried to remove at least some of the polar solvent.

"Cell extractant", as used herein, refers to any compound or combination of compounds that alters cell membrane or cell wall permeability or disrupts the integrity of (i.e., lyses or causes the formation of pores in) the membrane and/or cell wall of a cell (e.g., a somatic cell or a microbial cell) to effect extraction or release of a biological analyte normally found in living cells.

"Detection system", as used herein, refers to the components used to detect a biological analyte and includes enzymes, enzyme substrates, binding partners (e.g. antibodies or receptors), labels, dyes, and instruments for detecting light absorbance or reflectance, fluorescence, and/or luminescence (e.g. bioluminescence or chemiluminescence).

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a housing that comprises "a" detection reagent can be interpreted to mean that the housing can include "one or more" detection reagents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4B shows a cross-sectional view of the assembled device of FIG. 4A with the drain valve in an open configuration and the plunger disposed in a first position in the housing.

FIG. 4C shows a cross-sectional view of the assembled device of FIG. 4B with the plunger disposed in a second position in the housing and the cell concentration agent transferred to the second receptacle of the housing.

FIG. 4D shows a cross-sectional view of the device of FIG. 4C, wherein the plunger has punctured the frangible seals and transferred the cell concentration agent to the lower receptacle.

FIGS. 7B-7D show a cross-sectional views of the assembled device of FIG. 7A with the plunger inserted to various depths into the housing.

FIG. 8A shows an exploded side view, partially in section, of the tip of the plunger of FIG. 7A.

FIG. 8B shows a side view, partially in section, of the assembled tip of FIG. 8A.

DETAILED DESCRIPTION

Figures 1A, 1B, 1C, 1D:
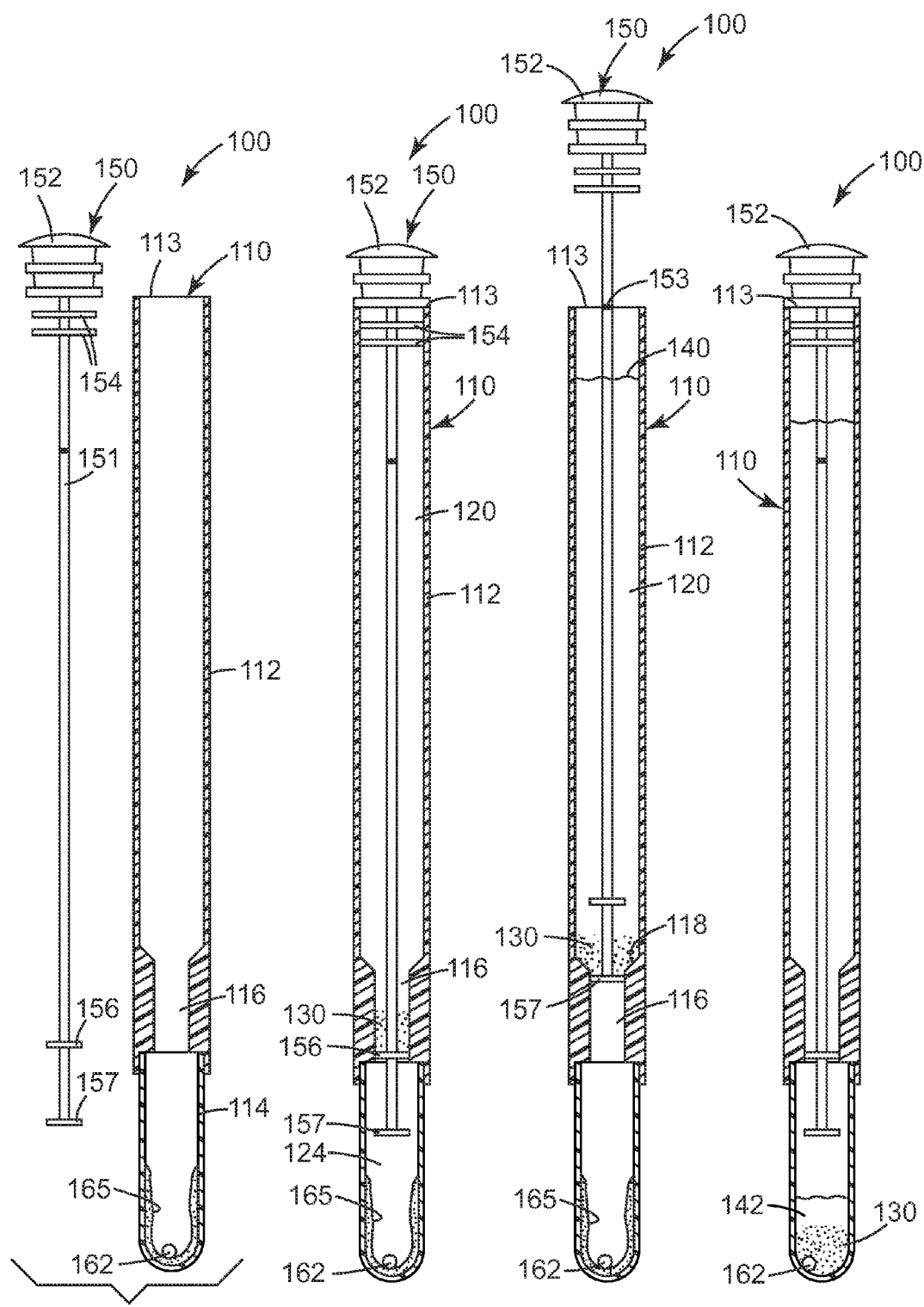
FIG. 1A shows a cross-sectional view of one embodiment of a housing comprising two receptacles and a cross-sectional view of a plunger adapted for use with the housing, which are both components of a sample preparation and detection device according to the present disclosure.
FIG. 1B shows a cross-sectional view of the assembled device of FIG. 1A with the plunger disposed in the housing in a first position and including a cell concentration agent in a upper receptacle of the housing.
FIG. 1C shows a cross-sectional view of the device of FIG. 1B with the plunger disposed in the housing in a second position and including a liquid sample in the upper receptacle of the housing.
FIG. 1D shows a cross-sectional view of the device of FIG. 1C with the plunger in the first position and the cell concentration agent in a lower receptacle of the housing.

All patents, patent applications, government publications, government regulations, and literature references cited in this specification are hereby incorporated herein by reference in their entirety. In case of conflict, the present description, including definitions, will control.

The present invention generally relates to articles and methods for detecting microorganisms in a sample. In certain preferred embodiments, the present invention relates to the detection of live microorganisms in a sample. Methods and devices for the concentration of cells from a sample are described in International Publication Nos. WO2010/078399 and WO2010/078404, each incorporated herein by reference in its entirety. The inventive devices and methods disclosed herein provide increased sensitivity to detect small numbers of microorganisms present in a sample.

Biological analytes can be used to detect the presence of biological material, such as live cells in a sample. Biological analytes can be detected by various reactions (e.g., binding reactions, catalytic reactions, and the like) in which they can participate.

Chemiluminescent reactions can be used in various forms to detect cells, such as bacterial cells, in fluids and in processed materials. In some embodiments of the present disclosure, a chemiluminescent reaction based on the reaction of adenosine triphosphate (ATP) with luciferin in the presence of the enzyme luciferase to produce light provides the chemical basis for the generation of a signal to detect a biological analyte, ATP. Since ATP is present in all living cells, including all microbial cells, this method can provide a rapid assay to obtain a quantitative or semiquantitative estimate of the number of living cells in a sample. Early discourses on the nature of the underlying reaction, the history of its discovery, and its general area of applicability, are provided by E. N. Harvey (1957), A History of Luminescence: From the Earliest Times Until 1900, Amer. Phil. Soc., Philadelphia, Pa.; and W. D. McElroy and B. L. Strehler (1949), *Arch. Biochem. Biophys.* 22:420-433.

ATP detection is a reliable means to detect bacteria and other microbial species because all such species contain some ATP. Chemical bond energy from ATP is utilized in the bioluminescent reaction that occurs in the tails of the firefly *Photinus pyralis*. The biochemical components of this reaction can be isolated free of ATP and subsequently used to detect ATP in other sources. The mechanism of this firefly bioluminescence reaction has been well characterized (DeLuca, M., et al., 1979 *Anal. Biochem.* 95:194-198).

Samples and Sample Acquisition Devices:

Articles and methods of the present disclosure provide for the detection of biological analytes in a sample. In some embodiments, the articles and methods provide for the detection of biological analytes from live cells in a sample. In certain embodiments, the articles and methods provide for the detection of live microbial cells in a sample. In certain preferred embodiments, the articles and methods provide for the detection of live bacterial cells in a sample.

The term "sample" as used herein, is used in its broadest sense. A sample is a composition suspected of containing a biological analyte (e.g., ATP) that is analyzed using the invention. The biological analyte may be present in a cell (e.g. a bacterium) in the sample. While often a sample is known to contain or suspected of containing a cell or a population of cells, optionally in a growth media, or a cell lysate, a sample may also be a solid surface, (e.g., a swab, membrane, filter, particle), suspected of containing an attached cell or population of cells. It is contemplated that for such a solid sample, an aqueous sample is made by contacting the solid with a liquid (e.g., an aqueous solution) which can be mixed with cell concentration agents according to the present invention.

Suitable samples include samples of solid materials (e.g., particulates, filters), semisolid materials (e.g., a gel, a liquid suspension of solids, or slurry), a liquid, or combinations thereof. Suitable samples further include surface residues comprising solids, liquids, or combinations thereof. Nonlimiting examples of surface residues include residues from environmental surfaces (e.g., floors, walls, ceilings, fomites, equipment, water, and water containers, air filters), food surfaces (e.g., vegetable, fruit, and meat surfaces), food processing surfaces (e.g., food processing equipment and cutting boards), and clinical surfaces (e.g., tissue samples, skin and mucous membranes). Samples can also include mixtures such as crude or partially-refined oil, gasoline, or paint.

The collection of sample materials, including surface residues, for the detection of biological analytes is known in the art. Various sample acquisition devices, including pipettes, spatulas, sponges, swabs and the like have been described and can be used in the methods of the present invention.

Cell Concentration Agents:

Methods of the present disclosure include the use of cell concentration agents to couple with cells that are present in a liquid sample. The cell concentration agent is contacted for a period of time with a liquid sample suspected of containing cells. The cells can be coupled to the cell concentration agent either covalently, noncovalently (e.g., by hydrophobic or ionic interactions), or by a combination of covalent and noncovalent coupling. After the cells have coupled to the cell concentration agent, the cell concentration agent can be removed from the liquid sample by, for example, sedimentation, flocculation, centrifugation, filtration or any combination of the foregoing.

"Cell concentration agent" is used broadly to include materials (e.g., particles, fibers) that can be suspended in a liquid and, thereby, capture and retain microorganisms that are present in the liquid. Although cell concentration agents can be collected by a filtration process, they do not necessarily require a filtration process to capture the microorganisms.

Certain cell concentration agents are known in the art and are suitable for use in methods of the present disclosure. Nonlimiting examples of suitable cell concentration agents include hydroxyapatite (Berry et al.; Appl. Environ. Microbiol.; 63:4069-4074; 1997), magnetic beads (Oster et al., J. Magnetism and Magnetic Mat.; 225:145-150; 2001), ferrimagnetic mineral, magnetite, chitosan, and affinity supports. The use of compositions including an immobilized-metal support material to capture or concentrate microorganisms from a sample is described in International Publication No. WO2008/134472, which is incorporated herein by reference in its entirety.

One exemplary type of concentration agents include diatomaceous earth and surface treated diatomaceous earth. Specific examples of such concentration agents can be found in commonly assigned International Publication No. WO2009/046191; the disclosure of which is incorporated herein by reference. When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). In an embodiment, concentration agents can have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged.

One exemplary type of concentration agent includes diatomaceous earth. Another exemplary type of concentration agent includes surface treated diatomaceous earth. Exemplary surface treatment includes a surface modifier, such as titanium dioxide, fine-nanoscale gold or platinum, or a combination thereof. Such surface treatments can be surprisingly more effective than untreated diatomaceous earth in concentrating microorganisms. The surface treatment can also further include a metal oxide selected from ferric oxide, zinc oxide, aluminum oxide, and the like, and combinations thereof. In an embodiment, ferric oxide is utilized. Although noble metals such as gold have been known to exhibit antimicrobial characteristics, the gold-containing concentration agents can be effective not only in binding the microorganisms but also in leaving them viable for purposes of detection or assay.

Useful surface modifiers include fine-nanoscale gold; fine-nanoscale platinum; fine-nanoscale gold in combination with at least one metal oxide (for example, titanium dioxide, ferric oxide, or a combination thereof); titanium dioxide; titanium dioxide in combination with at least one other (that is, other than titanium dioxide) metal oxide; and the like; and combinations thereof. In an embodiment, surface modifiers such as fine-nanoscale gold; fine-nanoscale platinum; fine-nanoscale gold in combination with at least ferric oxide or titanium dioxide; titanium dioxide; titanium dioxide in combination with at least ferric oxide; or combinations thereof can be utilized.

In an embodiment surface modifiers such as the following can be utilized: fine-nanoscale gold; fine-nanoscale platinum; fine-nanoscale gold in combination with ferric oxide or titanium dioxide; titanium dioxide; titanium dioxide in combination with ferric oxide; and combinations thereof. In an embodiment, fine-nanoscale gold; fine-nanoscale gold in combination with ferric oxide or titanium dioxide; titanium dioxide in combination with ferric oxide; and combinations thereof can be utilized. Fine-nanoscale gold, fine-nanoscale gold in combination with ferric oxide or titanium dioxide, and combinations thereof can also be utilized in an embodiment.

Another exemplary type of concentration agent includes gamma-FeO(OH) (also known as lepidocrocite). Specific examples of such concentration agents can be found in commonly assigned International Publication No. WO2009/046183; the disclosure of which is incorporated herein by reference. Such concentration agents have been found to be surprisingly more effective than other iron-containing concentration agents in capturing gram-negative bacteria, which can be of great concern in regard to food- and water-borne illnesses and human bacterial infections. The concentration agents can further include (in addition to gamma-FeO(OH)) other components (for example, boehmite ($\alpha$-AlO(OH)), clays, iron oxides, and silicon oxides). In embodiments where such other components are included, they generally do not significantly interfere with the intimate contact of the sample and the concentration agent.

Gamma-FeO(OH) is known and can be chemically synthesized by known methods (for example, by oxidation of ferrous hydroxide at neutral or slightly acidic pHs, as described for purposes of magnetic tape production in U.S. Pat. No. 4,729,846 (Matsui et al.), the description of which is incorporated herein by reference). Gamma-FeO(OH) is also commercially available (for example, from Alfa Aesar, A Johnson Matthey Company, Ward Hill, Mass., and from Sigma-Aldrich Corporation, St. Louis, Mo.).

In an embodiment that utilized gamma-FeO(OH) as a concentration agent, the gamma-FeO(OH) is generally in the form of microparticles. In an embodiment, it is in the form of microparticles having particle sizes (largest dimension) in the range of about 3 micrometers (in other embodiments, about 5 micrometers; or about 10 micrometers) to about 100 micrometers (in other embodiments, about 80 micrometers; or about 50 micrometers; or about 35 micrometers; where any lower limit can be paired with any upper limit of the range). In an embodiment, the particles are agglomerates of smaller particles. The particles can include crystallites that are less than about 1 micrometer in size (in an embodiment, less than about 0.5 micrometer in size). The crystallites can be present as acicular crystallites, as raft-like structures comprising acicular crystallites, or as combinations of the acicular crystallites and raft-like structures.

In an embodiment, the concentration agents have a surface area as measured by the BET (Brunauer-Emmett-Teller) method (calculation of the surface area of solids by physical adsorption of nitrogen gas molecules) that is greater than about 25 square meters per gram ($m^2/g$); in an embodiment greater than about 50 $m^2/g$; and in another embodiment greater than about 75 $m^2/g$.

An agglomerated form of the particles can provide the adsorptive capabilities of fine particle systems without the handling and other hazards often associated with fine particles. In addition, such agglomerate particles can settle readily in fluid and thus can provide rapid separation of microorganisms from a fluid phase (as well as allowing low back pressure when filtered).

Another exemplary type of concentration agents includes metal silicates. Specific examples of such concentration agents can be found in commonly assigned International Publication No. WO2009/085357; the disclosure of which is incorporated herein by reference. Exemplary metal silicates can have a surface composition having a metal atom to silicon atom ratio of less than or equal to about 0.5 (in an embodiment, less than or equal to about 0.4; in another embodiment, less than or equal to about 0.3; in yet another embodiment, less than or equal to about 0.2), as determined by X-ray photoelectron spectroscopy (XPS). In an embodiment, the surface composition also includes at least about 10 average atomic percent carbon (in an embodiment, at least about 12 average atomic percent carbon; in yet another embodiment at least about 14 average atomic percent carbon), as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Exemplary surface composition assessment conditions for XPS can include a take-off angle of 90 degrees measured with respect to the sample surface with a solid angle of acceptance of ±10 degrees.

When dispersed or suspended in water systems, inorganic materials such as metal silicates exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). Exemplary concentration agents can have zeta potentials that are more negative than that of, for example, a common metal silicate such as ordinary talc. Yet the concentration agents are surprisingly more effective than talc in concentrating microorganisms such as bacteria, the surfaces of which generally tend to be negatively charged. In an embodiment, the concentration agents have a negative zeta potential at a pH of about 7 (in an embodiment, a Smoluchowski zeta potential in the range of about −9 millivolts to about −25 millivolts at a pH of about 7; in another embodiment, a Smoluchowski zeta potential in the range of about −10 millivolts to about −20 millivolts at a pH of about 7; in yet another embodiment a Smoluchowski zeta potential in the range of about −11 millivolts to about −15 millivolts at a pH of about 7).

Useful metal silicates include, but are not limited to, amorphous silicates of metals such as magnesium, calcium, zinc, aluminum, iron, titanium, and the like, and combinations thereof. In an embodiment, magnesium, zinc, iron, titanium, or combinations thereof can be utilized. In yet another embodiment, magnesium is utilized. In an embodiment, amorphous metal silicates in at least partially fused particulate form can be utilized. In an embodiment, amorphous, spheroidized metal silicates can be utilized. In yet another embodiment, amorphous, spheroidized magnesium silicate can be utilized. Metal silicates are known and can be chemically synthesized by known methods or obtained through the mining and processing of raw ores that are naturally-occurring.

Some amorphous metal silicates are commercially available. For example, amorphous, spheroidized magnesium silicate is commercially available for use in cosmetic formulations (for example, as 3M Cosmetic Microspheres CM-111, available from 3M Company, St. Paul, Minn.).

In addition to amorphous metal silicates, the concentration agents can also include other materials including oxides of metals (for example, iron or titanium), crystalline metal silicates, other crystalline materials, and the like, provided that the concentration agents have the above-described surface compositions. In an embodiment, a concentration agent contains essentially no crystalline silica.

The concentration agents can be used in any form that is amenable to sample contact and microorganism capture. In an embodiment, the concentration agents are used in particulate form. In an embodiment, the concentration agent is in the form of microparticles. In an embodiment, the concentration agent is in the form of microparticles having a particle size in the range of about 1 micrometer (in an embodiment, about 2 micrometers) to about 100 micrometers (in an embodiment, about 50 micrometers; in another embodiment, about 25 micrometers; in yet another embodiment about 15 micrometers; where any lower limit can be paired with any upper limit of the range).

Microbial concentration or capture using concentration agents is generally not specific to any particular strain, species, or type of microorganism and therefore provides for the concentration of a general population of microorganisms in a sample. Specific strains of microorganisms can then be detected from among the captured microorganism population using any known detection method with strain-specific probes. Thus, the concentration agents can be used for the detection of microbial contaminants or pathogens (particularly food-borne pathogens such as bacteria) in clinical, food, environmental, or other samples.

In carrying out the process of the invention, the concentration agents can be used in any form that is amenable to sample contact and microorganism capture (for example, in particulate form or applied to a support such as a dipstick, film, filter, tube, well, plate, beads, membrane, or channel of a microfluidic device, or the like). Preferably, the concentration agents are used in particulate form.

Optionally, the cell concentration agent may comprise a binding partner (e.g., an antibody, an antibody fragment, an antigen-binding domain, a lectin (e.g., Concanavalin A), a receptor, a phage receptor, or the like), which can couple to a microorganism. The coupling can be direct or indirect. The coupling can be selective for certain microorganism types or it can be nonselective.

The amount of concentration agent used to capture microorganisms from a sample can depend at least in part on the type of concentration agent utilized, the sample size, the receptacle type and size, sample mixing, the particular application, other factors not specifically discussed herein, or a combination thereof. The capture efficiency (the percent of microorganisms in the sample bound to concentration agent) can generally be increased by allowing increased time for the microorganism to come in contact with the concentration agent. The capture efficiency can also be increased by having a higher concentration of concentration agent, which decreases the mean diffusion distance a microorganism must travel to be captured, leading to a shorter incubation time. Therefore, as a generality, the more concentration agent added, the shorter incubation time necessary to capture the same amount of microorganisms.

In an embodiment, an appropriate amount of concentration agent can vary given the time necessary to wait for the microorganisms to be bound to the concentration agent (referred to as "capture time"). For example, for a capture time of 1 minute, 1000 mg of concentration agent per 10 mL of sample could be appropriate; for a capture time of 10 minutes, 100 mg of concentration agent per 10 mL of sample could be appropriate; and for a capture time of 60 minutes, 10 mg of concentration agent per 10 mL of sample could be appropriate. In an embodiment, from about 1 mg to about 100 mg of concentration agent per 10 mL of sample can be utilized. In an embodiment, from about 1 mg to about 50 mg of concentration agent per 10 mL of sample can be utilized. In an embodiment, from about 10 mg to about 25 mg of concentration agent per 10 mL of sample can be utilized. In an embodiment utilizing a metal silicate concentration agent for example, about 10 mg of a metal silicate concentration agent per 10 mL of sample can be utilized. In an embodiment utilizing a metal silicate concentration agent for example, about 25 mg of a metal silicate concentration agent per 10 mL of sample can be utilized.

Detection Devices:

The present disclosure provides devices that can be used to detect microorganisms in a sample. The devices can include a housing comprising at least two receptacles with a passageway therebetween, an optional cell concentration agent disposed in an upper receptacle of the housing, a means for isolating at least two receptacles in the housing, and means for transferring the cell concentration agent from the upper receptacle to a lower receptacle of the housing. In some embodiments, the housing can include the means (e.g. a frangible seal) for isolating the two receptacles. In some embodiments, the housing can include the means (e.g., a valve) for transferring the cell concentration agent from the upper receptacle to the lower receptacle of the housing. In some embodiments, the devices further can include a reagent for detecting microorganisms. In certain embodiments, the devices further can include a hydrogel comprising a cell extractant. The cell extractant can facilitate the detection of a biological analyte from the microorganism.

Turning now to the drawings, FIG. 1A shows a cross-sectional view of the components of one embodiment of a detection device 100 according to the present disclosure. The detection device 100 components comprise a housing 110 and a plunger 150. The housing 110 includes an upper part 112 adjacent a lower part 114. The upper part 112 and lower part 114 can be formed separately from polymeric material, such as polyethylene or polypropylene, by processes that are well-known in the art such as, for example, molding. The parts can be dimensioned such that they can be press-fit together to provide a substantially liquid-tight coupling or, alternatively, they can be coupled together by means that are known in the art (e.g., by an adhesive, sonic welding, or the like). Alternatively, the housing could be formed as a single unit by processes that are known in the art, such as extruding a hollow body, molding the passageway, and sealing the bottom of the housing with a process involving heat, for example. In other embodiments, an insert part, comprising the narrow passageway, could be placed into a unitary housing to form the upper and lower receptacles (120 and 124, respectively).

At the end of the upper part 112 distal the lower part 114, is an opening 113 that is dimensioned to receive the plunger 150. At the opposite end of the upper part 112 is a passageway 116 that opens into the lower part 114 of the housing 110. In the illustrated embodiment, the passageway 116, which has a cross-sectional area that is smaller than the cross-sectional area of the upper receptacle 120, is shown as an inward extension of the wall that forms the upper part 112. Alternatively, the passageway 116 could be formed by an insert that fits inside the wall of the upper part 112 adjacent the lower part 114 of the housing 110 (not shown). The insert could form the passageway 116 adjacent the lower part 114 of the housing 110. The relative proportions of the upper part 112, lower part 114, and passageway 116 in FIG. 1A are merely illustrative and can be adapted, as necessary to accommodate various parameters, such as sample volume and/or instrument limitations.

The plunger 150 comprises a shaft 151 with a handle 152 at one end and a plurality of seals (first lower seal 156 and second lower seal 157) at the opposite end. Optionally, the plunger 150 can comprise one or more upper seals 154 and/or an index mark 153. The relative distances between the handle 152, first lower seal 156 and second lower seal 157 are described below. Also shown in FIG. 1A is optional detection reagent 165 and optional hydrogel 162.

"Detection reagent" is used herein in its broadest sense. A detection reagent is a reagent that can be used in a reaction to detect a biological analyte. Nonlimiting examples of detection reactions include interaction between binding partners (e.g., antigen-antibody, receptor-ligand, probe-target, and hybridization binding interactions) and/or catalytic reactions (e.g., enzyme-mediated reactions such as, for example, fluorogenic reactions, chromogenic reactions, lumigenic reactions, or polymerization reactions). Detection reagents may participate (e.g., as a binding partner, an enzyme, an enzyme substrate, or an indicator) in the detection reaction and/or may facilitate (e.g., as a buffer, a cofactor, or a component of a coupled reaction) a detection reaction. Exemplary detection reagents include enzymes, including, for example, luciferase, adenylate kinase, peroxidase, alkaline phosphates, apyrase, and the like; enzyme substrates, including, for example, luciferin, methylumbelliferyl phosphate, o-nitrophenylphosphate, p-nitrophenylphosphate, and 5-bromo-4-choloro-3-indoxyl-phosphate; buffers, including, for example, phosphate buffer, TRIS buffer, and HEPES buffer; and cofactors, including, for example, FADH, NADH, coenzyme A, and the like.

Detection reagents can be included in the housing 110 in various configurations. For example, the detection reagent 165 can comprise a dried or partially-dried coating, as shown in FIG. 1A. Suitable alternative configurations (not shown) for the detection reagent 165 are well known in the art and include, for example, liquid reagents (optionally, in a frangible compartment, such as an ampoule), powders, gels, tablets, lyophilized reagents, coated films, cakes, and drieddown reagents.

FIG. 1B shows a cross-sectional view of a detection device 100 comprising the housing 110 with the plunger 150 of FIG. 1A. This drawing illustrates a configuration in which the device 100 can be stored before use. The plunger 150 is fully-inserted in the housing 110. In this position, the lower edge of the handle 152 blocks the opening 113 of the upper part 112 of the housing 110, thereby preventing material from entering or exiting the housing 110. Optional upper seals 154 can also serve to prevent materials from entering or exiting the housing 110. The upper seals 154 are dimensioned to contact the inner surface of the wall of the upper part 112 of the housing 110 and are made of a suitable material (e.g., poly propylene, butyl rubber) to form a barrier, preferably a liquid-resistant barrier.

When the plunger 150 is in the position shown in FIG. 1B, the first lower seal 156 blocks the passageway 116, thereby isolating the upper receptacle 120 from the lower receptacle 124 of the housing 110. When the plunger 150 is in the position shown in FIG. 1B, a portion of the plunger 150 which includes the second lower seal 157 extends into the lower receptacle 124 and does not contact the walls of lower part 114 of the housing 110. The first lower seal 156 and second lower seal 157 are dimensioned to contact the walls of the passageway 116 and are made of a suitable material (e.g., poly propylene, butyl rubber) to form a barrier, preferably a liquid-resistant barrier in the passageway 116 between the upper receptacle 120 and the lower receptacle 124. Also shown in FIG. 1B is an optional concentration agent 130, located in the upper receptacle 120.

FIG. 1C shows a cross-sectional view of the device 100 of FIG. 1B with the plunger 150 in a second position. This plunger 150 position can be used, for example, to load a sample into the housing 110. The plunger 150 can be grasped by the handle 152 and withdrawn until the second lower seal 157 is proximate the upper end of the passageway 116. The optional index mark 153 on the plunger shaft 151 can be used (e.g., when it is aligned with the opening 113) to indicate the proper location of the plunger 150 to attain this position. FIG. 1C further comprises a liquid sample 140 that is contacting the concentration agent 130 in the upper receptacle 120. During use, the device 100 can be vortexed or vibrated, for example, to mix the concentration agent 130 and the liquid sample 140. After a period of time, the concentration agent 130 can settle to the bottom of the upper receptacle 120, as shown in FIG. 1C. In some embodiments, an optional taper region 118 is located adjacent the passageway 116. The taper region 118 can be formed from the same material and/or process as the upper part 112 of the housing 110 and/or the passageway 116. In use, the taper region 118 can direct toward the passageway 116 liquid-suspended particles (e.g., cell concentration agent 130) that are sedimenting toward the passageway 116 within the housing 110.

FIG. 1D shows a cross-sectional view of the device 100 of FIG. 1C with the plunger 150 returned to the first position shown in FIG. 1B. The lower edge of the handle 152 is proximate the opening 113 and a portion 142 of the liquid sample, containing the concentration agent 130 is transferred to the lower receptacle 124, where the portion 142 can interact with a detection reagent 165 (shown in FIG. 1A), if present. Non-limiting examples of interactions between the portion 142 and the detection reagent 165 include dissolution and/or suspension of the detection reagent, binding interactions between the detection reagent and a biological analyte present in the portion, and/or a catalytic reaction. FIG. 1D also shows the portion 142 of the liquid sample contacting the hydrogel 162 in the lower receptacle 124, which can result in the release of a cell extractant from the hydrogel 162.

In the embodiment illustrated in FIG. 1, the means for isolating the upper receptacle 120 from the lower receptacle 124 comprises the first lower seal 156 and/or second lower seal 157 of the plunger 150 in combination with the passageway 116. In the embodiment illustrated in FIG. 1, the means for transferring the concentration agent 130 from the upper receptacle 120 to the lower receptacle 124 includes the passageway 116 and the first lower seal 156 and second lower seal 157 of the plunger 150.

Figure 2A:
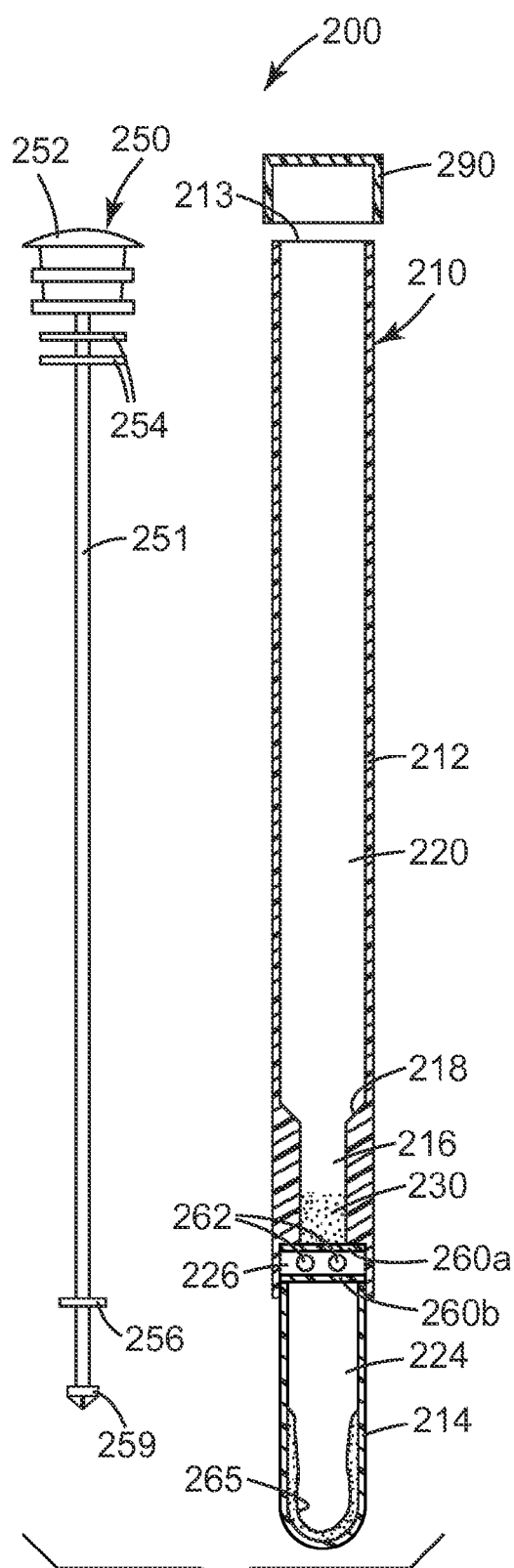
FIG. 2A shows a cross-sectional view of one embodiment of a housing comprising three receptacles separated by frangible seals and a side view of a plunger adapted for use with the housing, which are both components of a sample preparation and detection device according to the present disclosure.

FIG. 2A shows a cross-sectional view of a plunger 250 and a partially-exploded cross-sectional view of a housing 210, which are components of one embodiment of a detection device 200 according to the present invention. The housing 210 includes an upper part 212 adjacent a lower part 214. The upper part 212 and lower part 214 can be formed as described above.

At the end of the upper part 212 distal the lower part 214, is an opening 213 that is dimensioned to receive the plunger 250. At the opposite end of the upper part 212 is a passageway 216, as described above. Adjacent the passageway 216 is an optional taper region 218, as described herein. Frangible seals 260a and 260b divide the housing into the upper receptacle 220, lower receptacle 224, and third receptacle 226. Frangible seals 260a and 260b are preferably made from a water-resistant material (e.g., a thin polymeric film, a polymer-coated paper, a thin foil) and can be secured to the walls of the housing 210 using materials and/or processes that are known in the art (e.g., an adhesive, heat-sealing, ultrasonic welding) to form a water-resistant frangible barrier.

Located in the third receptacle 226 is a hydrogel 262 comprising a cell extractant. Suitable hydrogels comprising a cell extractant are described in International Publication No. WO2010/039627, which is incorporated herein by reference in its entirety.

The relative proportions of the three receptacles in FIG. 2A are merely illustrative and can be adapted, as necessary to accommodate various parameters, such as sample volume and/or instrument limitations. Also shown in FIG. 2A are an optional concentration agent 230, optional detection reagent 265 as described herein and optional removable cap 278. Cap 278 can be made from, for example, a polymeric material (e.g., polyethylene, polypropylene) using processes known in the art (e.g., molding) and can be dimensioned to form a liquid-resistant cover for the housing 210.

The plunger 250 comprises a shaft 251 with a handle 252 at one end and the lower seal 256 and piercing end 259 at the opposite end. Preferably, the lower seal 256 dimensioned to contact the walls of the passageway 216 and is made of a suitable material (e.g., poly propylene, butyl rubber) to form a barrier, preferably a liquid-resistant barrier, in the passageway 216. Optionally, the plunger 250 can comprise one or more upper seals 254 as described above. The relative distances between the handle 252, lower seal 256 and the piercing end 259 are described below.

Figure 2B:
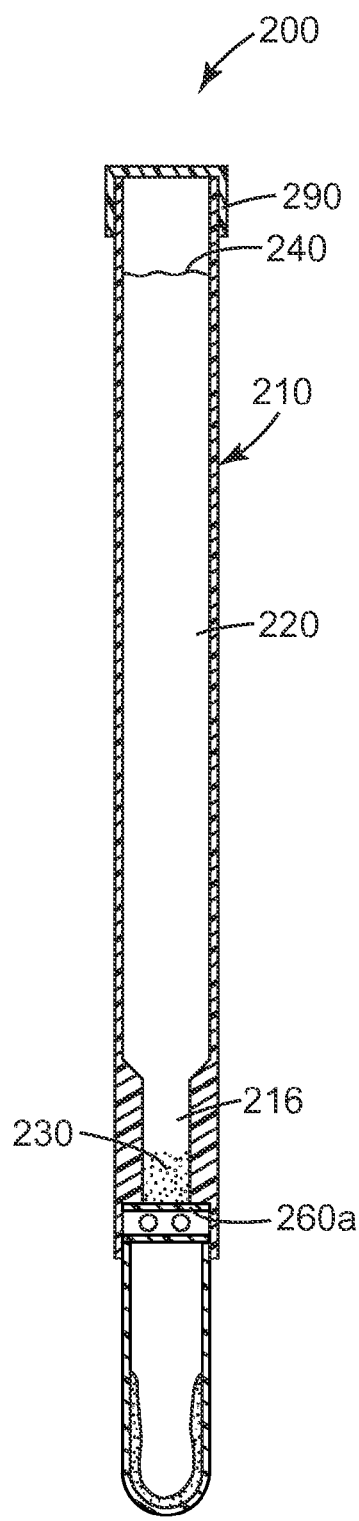
FIG. 2B shows a cross-sectional view of the housing of FIG. 2A with a cap secured thereon and with a liquid sample disposed in an upper receptacle of the housing.

FIG. 2B shows a cross-sectional view of the device 200 of FIG. 2A. In this view, the housing 210 further comprises a liquid sample 240 in the upper receptacle 220. The cap 278 is firmly seated on the housing 210 and, thus, the liquid sample 240 can be mixed with the cell concentration agent 230 by processes that are known in the art such as, for example, vortexing, vibrating, shaking, or inverting the housing 210. After mixing, the cell concentration agent 230 can be allowed to settle onto the frangible seal 260a in the passageway 216.

Figure 2C:
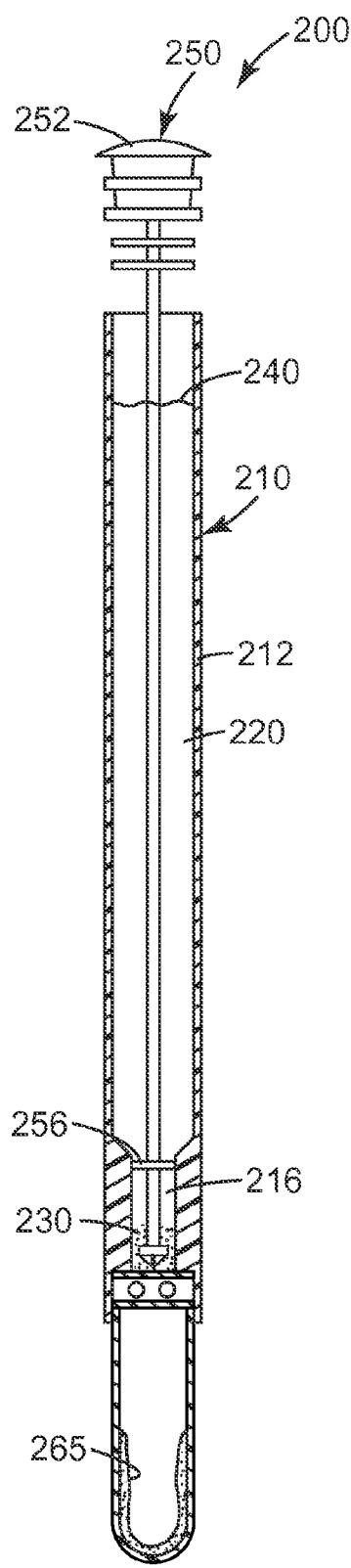
FIG. 2C shows a cross-sectional view of the housing of FIG. 2B without the cap and with a plunger disposed in a first position in the housing.

FIG. 2C shows a cross-sectional view of the device 200 comprising the housing 210 of FIG. 2B with a plunger 250 partially inserted therein. In this position, the lower seal 256 of the plunger 250 contacts the walls of the passageway 216, thereby isolating in the passageway 216 at least a portion 242 from the rest of the liquid sample 240. Also isolated in the passageway 216 is the cell concentration agent 230.

Figure 2D:
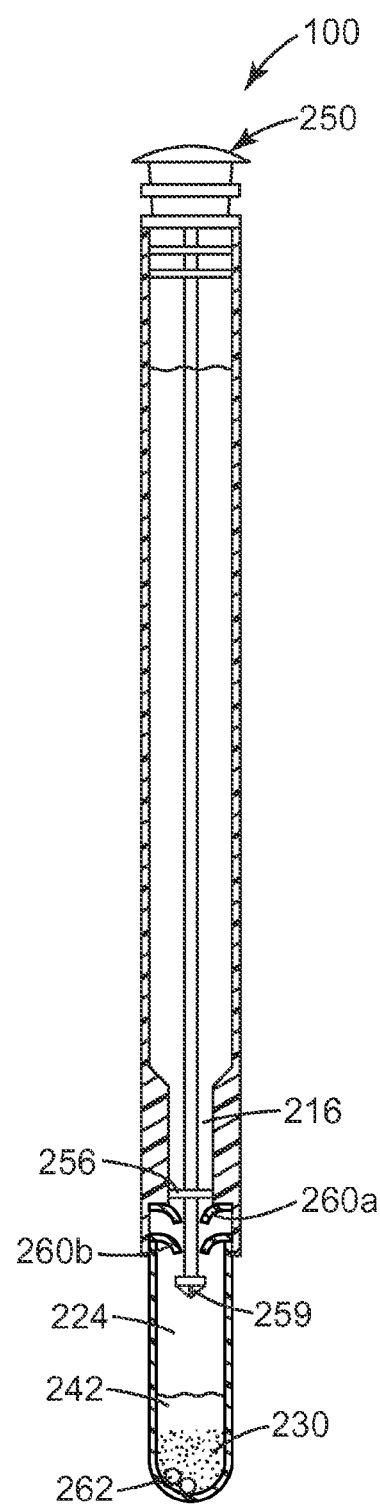
FIG. 2D shows a cross-sectional view of the device of FIG. 2C with the plunger disposed in a second position in the housing and the cell concentration agent transferred to the lower receptacle of the housing.

FIG. 2D shows a cross-sectional view of the device 200 of FIG. 2C with the plunger 250 fully inserted therein. The lower seal 256 of the plunger 250 contacts the walls of the passageway 216 and the piercing end 259 has punctured frangible seals 260a and 260b, thereby transferring the portion 242 of the liquid sample, the cell concentration agent 230, and the hydrogel 262 into the lower receptacle 224, where the portion 242 can interact with optional detection reagent 265 (shown in FIG. 2A), if present. Non-limiting examples of interactions between the portion 242 and the detection reagent 265 include dissolution and/or suspension of the detection reagent, binding interactions between the detection reagent and a biological analyte present in the portion, and/or a catalytic reaction.

In the illustrated embodiment of FIG. 2, the means for isolating the upper receptacle 220 from the lower receptacle 224 includes the frangible seals 260a and 260b. Means for isolating the upper receptacle 220 from the lower receptacle 224 can also include the lower seal 256 of the plunger 250 in combination with the passageway 216. In the illustrated embodiment of FIG. 2, the means for transferring the cell concentration agent 230 from the upper receptacle 220 to the lower receptacle 224 includes the piercing end 259 and lower seal 256 of the plunger 250 and the passageway 216.

Figures 3A, 3B:
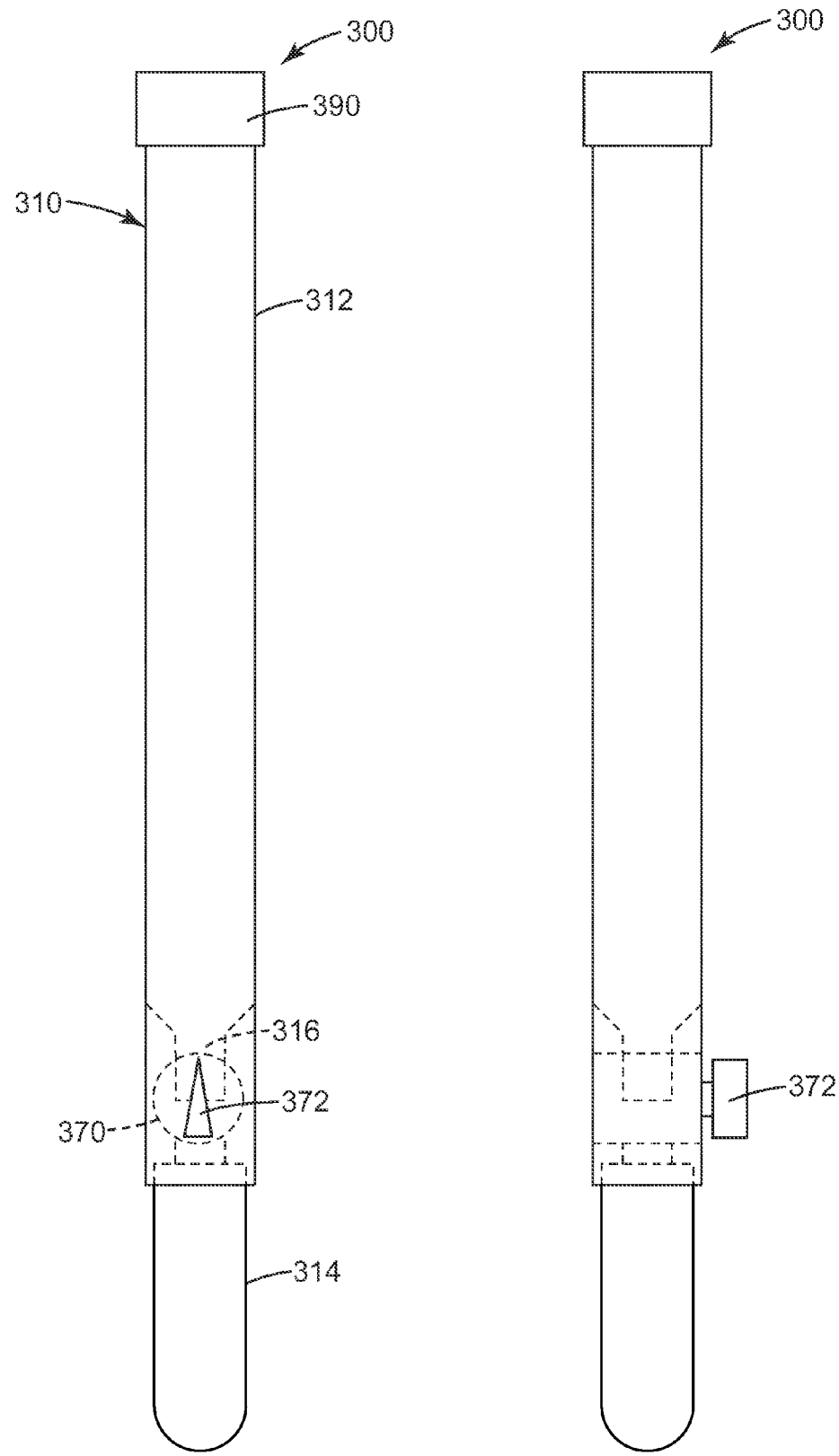
FIG. 3A shows a front view of one embodiment of a sample preparation and detection device comprising a housing and a valve, according to the present disclosure.
FIG. 3B shows a side view of the device of FIG. 3A.

FIG. 3A shows a front view of one embodiment of a detection device 300 according to the present disclosure. The device 300 includes a housing 310 and an optional cap 378. The housing 310 can be constructed as described above with an upper part 312, a passageway 316, and a lower part 314. The optional cap 378 can be constructed as described above. The device 300 also includes a dead-end valve 370 with a valve actuator 372, which is shown in a first position in FIG. 3A. FIG. 3B shows a side view of the device 300 and valve actuator 372 of FIG. 3A.

Figures 3C, 3D:
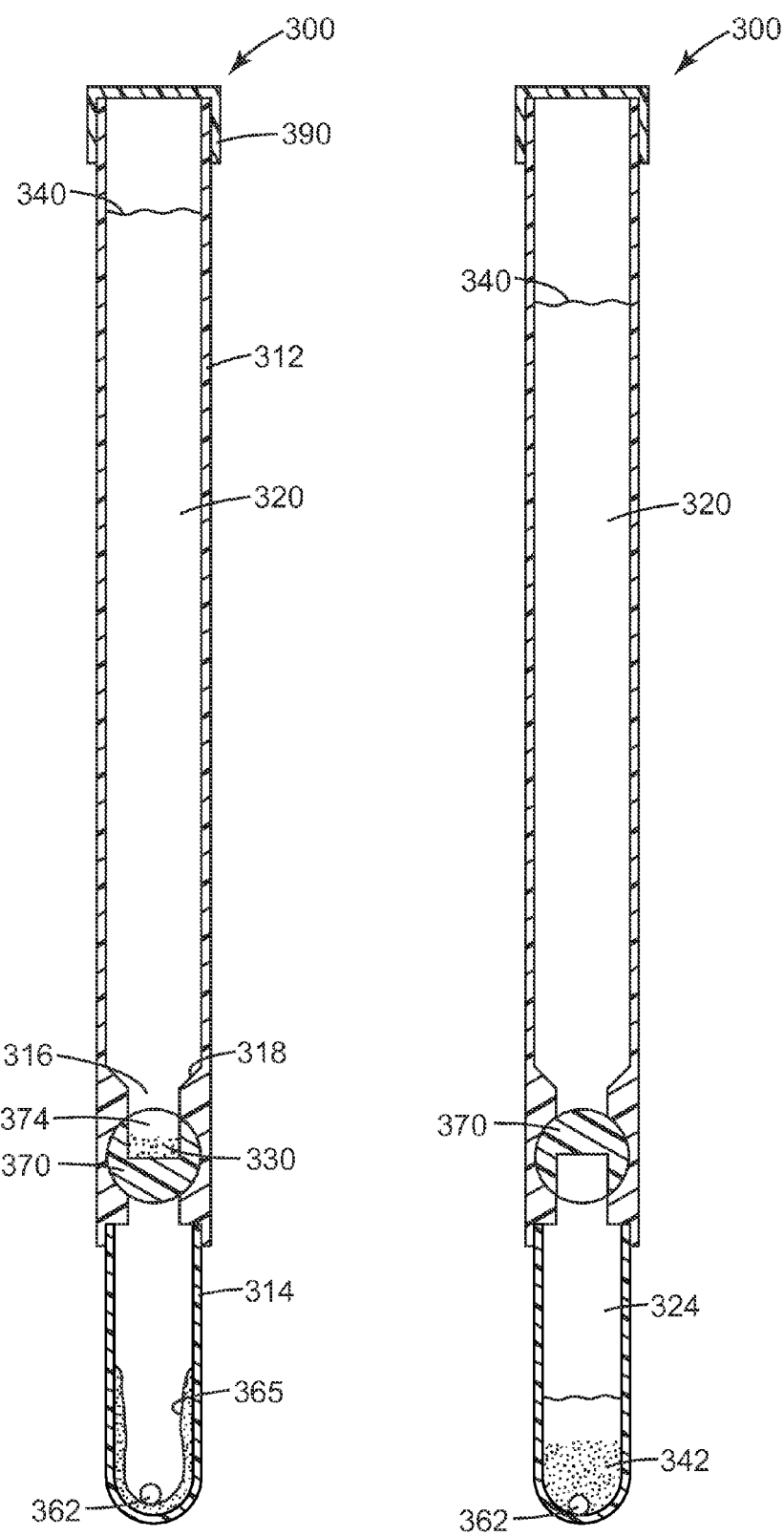
FIG. 3C shows a cross-sectional view of the device of FIG. 3A with a liquid sample and a cell concentration agent disposed in a upper receptacle of the housing and the valve in a first position.
FIG. 3D shows a cross-sectional view of the device of FIG. 3C with the valve in a second position and the cell concentration agent transferred to the lower receptacle of the housing.

FIG. 3C show a cross-sectional view of the device 300 shown in FIG. 3A. The device 300 comprises a cap 378 and a housing 310. The housing 310 includes an upper part 312 and lower part 314. The upper part 312 includes a passageway 316 in which a dead-end valve 370 is positioned. The dead-end valve 370 includes a valve cavity 374 which, when the valve is in this first position, is in fluid communication with the upper receptacle 320. The valve cavity 374 includes an optional cell concentration agent 330, which contacts a liquid sample 340 in the upper receptacle 320. The lower receptacle 324 contains an optional hydrogel 362 and/or optional detection reagent 365, both as described herein. Also shown in FIG. 3C is optional taper region 318, as described herein.

FIG. 3D shows a cross-sectional view of the device 300 from FIG. 3C with the valve 370 in a second position. When the valve 370 is in the second position, a portion 342 of the liquid sample, containing the cell concentration agent 330, is isolated and transferred to the lower receptacle 324 where the portion 342 can contact the hydrogel 362, if present, and can interact with the detection reagent 365, if present, as described herein.

It is recognized that the dimensions of the valve cavity 374 can constitute a known predetermined volume and that, as such, the valve 370 can be used one or more times to transfer a predetermined amount of the liquid sample 340 from the upper receptacle 320 to the lower receptacle 324. Furthermore, it is recognized that, after the portion 342 of the liquid sample has been transferred from the upper receptacle 320 to the lower receptacle 324, the remainder of the liquid sample 340 in the upper receptacle 320 could be discarded and a different material (e.g., a diluent, a buffer, a liquid and/or powder reagent) can be placed into the upper receptacle 320 and a predetermined amount could subsequently be transferred to the lower receptacle 324 using the valve 370 (not shown).

In the illustrated embodiment of FIG. 3, the means for isolating the upper receptacle 320 and lower receptacle 324 of the housing includes the valve 370. In the illustrated embodiment of FIG. 3, the means for transferring the cell concentration agent 330 from the upper receptacle 320 to the lower receptacle 324 includes the passageway 316 and the valve 370.

Figure 4A:
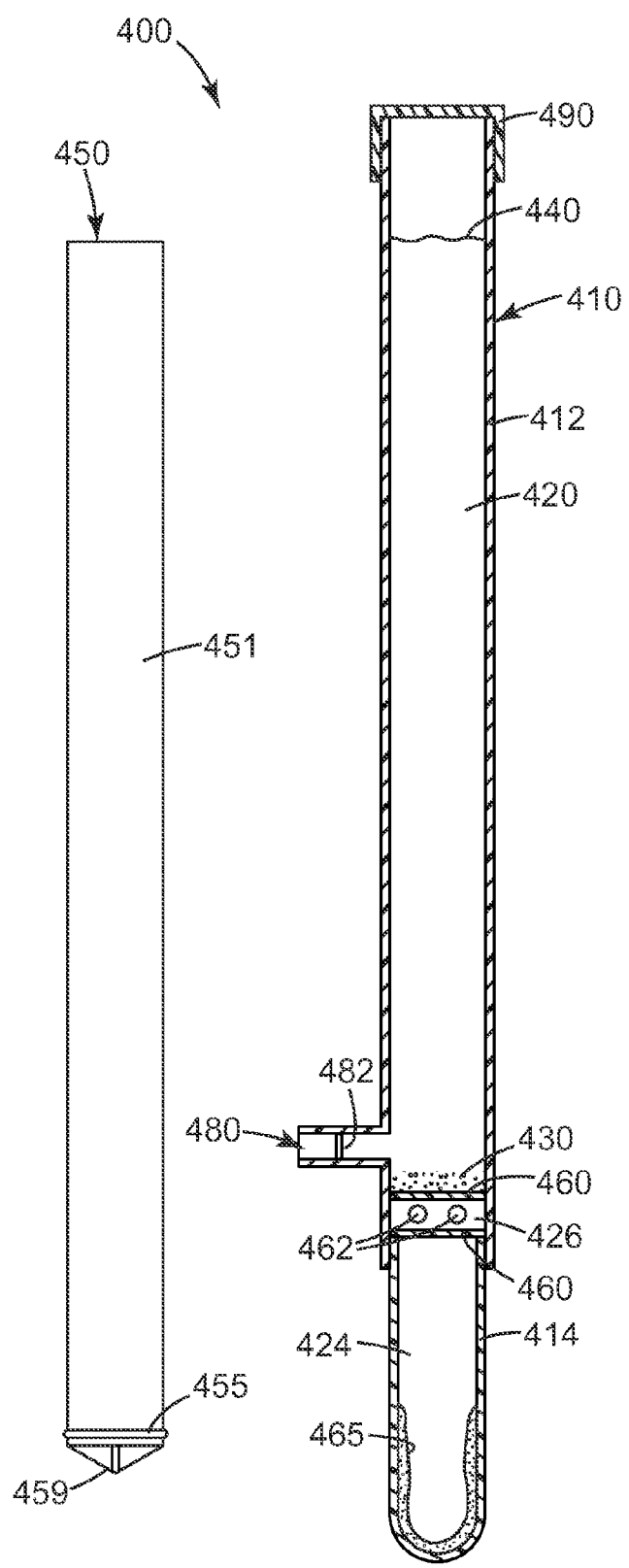
FIG. 4A shows a cross-sectional view of one embodiment of a housing comprising two receptacles and a drain valve and a side view of a plunger, which are both components of a sample preparation and detection device.

FIG. 4A shows a side view of a plunger 450 and a cross-sectional view of a housing 410, both of which are components of a detection device 400 according to the present disclosure. The plunger comprises a shaft 451, optional O-ring 455, and piercing end 459. The O-ring can be made of a conformable material (e.g., butyl rubber) to provide a liquid-tight seal with the housing 410. The housing 410 can be constructed as described above with an upper part 412 and a lower part 414. The optional cap 478 can be constructed as described above. Frangible seals 460 divide the housing 410 into three receptacles, an upper receptacle 420, lower receptacle 424, and third receptacle 426. In this illustration, frangible seals 460 are located at the end of the upper receptacle 420 that is proximate the lower receptacle 424. The space between the frangible seals 460 defines a third receptacle 426. Located in the third receptacle 426 is a hydrogel 462 comprising a cell extractant. An alternative construction (not shown) may have only one frangible seal 460 proximate the lower receptacle 424, with the hydrogel 462 located in the lower receptacle 424, as shown in FIG. 3C.

Located in the upper receptacle 420 proximate frangible seals 460 is a drain valve 480 with the valve gate 482, which is shown in the closed position. Also located in the upper receptacle 420 is the liquid sample 440 and the optional cell concentration agent 430. An optional detection reagent 465 is shown in the lower receptacle 424.

FIG. 4B shows a cross-sectional view of an assembled detection device 400 comprising the housing 410 and plunger 450 of FIG. 4A. The cell concentration agent 430 is settled to the bottom of the upper receptacle 420. The valve gate 482 of the drain valve 480 is in the open position and, as force is applied (e.g., by pressure from finger or hand) in the direction shown by the arrow, the clarified liquid sample 445 is expelled out of the drain valve 480. Also shown in FIG. 4B is detection reagent 465 coated on the wall of the lower receptacle 424.

FIG. 4C shows a cross-sectional view of the detection device 400 of FIG. 4B. In this view, the O-ring 455 and piercing end 459 of the plunger 450 are inserted in the housing 410 on the side of the drain valve 480 proximate the nearest frangible seal 460. In this position, the plunger 450 traps a portion 442 of the liquid sample comprising the cell concentration agent 430 between the plunger 450 and the nearest frangible seal 460.

FIG. 4D shows a cross-sectional view of the detection device 400 of FIG. 4C. In this view, the piercing end 459 of the plunger 450 has punctured both frangible seals 460 and the portion 442 of the liquid sample has transferred to the lower receptacle 424, where it has dissolved the detection reagent (shown in FIG. 4C) and the portion 442 is in contact with the hydrogel 462 comprising a cell extractant.

Figure 5A:
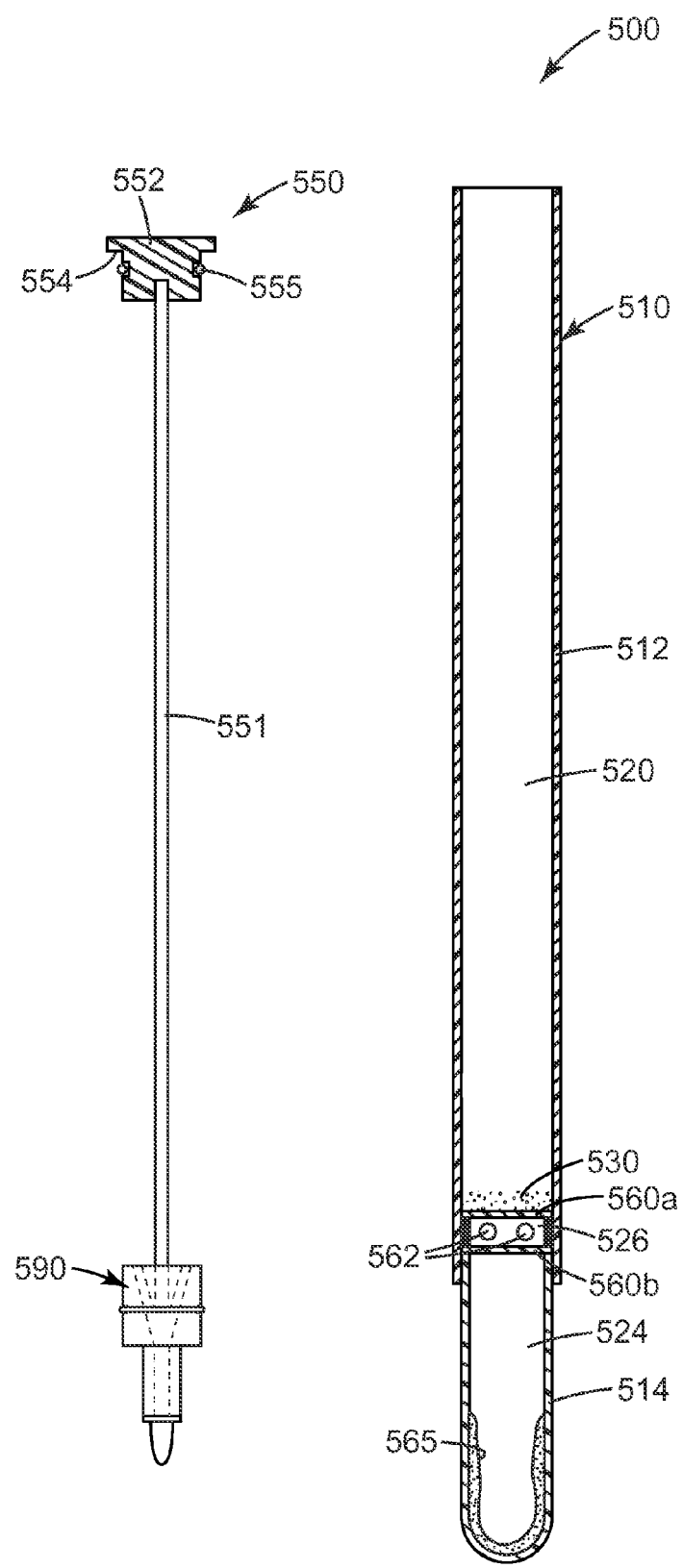
FIG. 5A shows a cross-sectional view of one embodiment of a housing and a side view of a plunger, partially in section, which are both components of one embodiment of a sample preparation and detection device according to the present disclosure.

FIG. 5A shows a cross-sectional view of a plunger 550 and a housing 510, both of which are components of a detection device 500. The plunger 550 comprises a shaft 551 with an optional handle 552 and a tip 590. In any embodiment, the handle 552 further may comprise an optional O-ring 555.

The housing 510 can be constructed as described above, with an upper part 512 and a lower part 514. Frangible seals 560a and 560b divide the housing 510 into three receptacles, an upper receptacle 520, lower receptacle 524, and third receptacle 526. In this illustration, frangible seals 560a and 560b are located at the end of the upper receptacle 520 that is proximate the lower receptacle 524. The space between the frangible seals 560a and 560b defines the third receptacle 526. Located in the third receptacle 526 is hydrogel 562, which comprises a cell extractant as described herein. In the illustrated embodiment, the lower receptacle 524 comprises an optional detection reagent 565. An alternative construction (not shown) may have only one frangible seal proximate the lower receptacle, with the hydrogel located in the lower receptacle, as shown in FIG. 3C.

The handle 552 can be made, using processes well known in the art, from a variety of materials including, for example, plastic, wood, metal, and combinations thereof. The optional O-ring 555 is disposed in a notch 554 in the handle 552. The handle 552 may be shaped and dimensioned such that at least a portion of the handle 552 can be inserted into the housing 510 when the plunger 550 is fully inserted in the housing 510. In one embodiment, the handle 552 further includes a rim 554 that engages the opening of the housing 510 to prevent the handle 552 from being fully inserted into the housing 510.

The shaft 551 of the plunger 550 can be made from a variety of materials including, for example, plastic, wood, metal, and combinations thereof. One end of the shaft 551 is coupled to the handle 552 by press-fitting into a recessed portion (as shown in FIG. 5), by ultrasonic welding, or by using an adhesive, for example. The other end of the shaft 551 is coupled to the tip 590 by press-fitting, by ultrasonic welding, or by using an adhesive, for example.

Figures 6A, 6B:
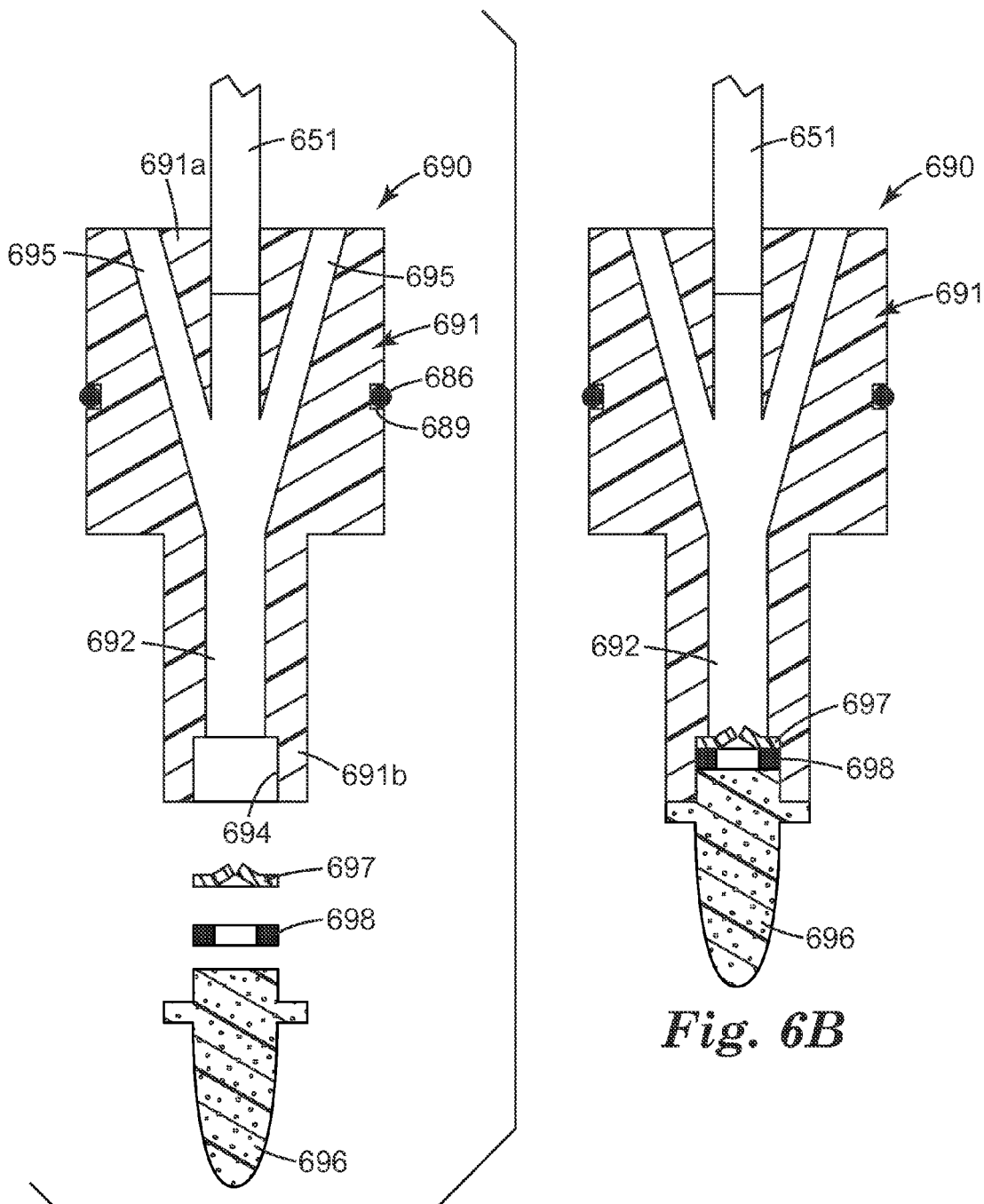
FIG. 6A shows an exploded side view, partially in section, of the tip of the plunger of FIG. 5A.
FIG. 6B shows a side view, partially in section, of the assembled tip of FIG. 6A.

Detail of the tip 590 of the plunger 550 is shown in FIGS. 6A and 6B.

FIG. 6A shows a partially exploded side view, partially in section, of the tip 590 of FIG. 5A. The tip 690 comprises a body 691, a one-way valve 697, and a filter 696.

The body 691 includes a first end 691a, a second end 691b, and a conduit 692 running through the body 691 from the first end 691a to the second end 691b. At the first end 691a, the conduit 692 is sealed by the shaft 651 of the plunger. At the second end 691b, the conduit 692 opens into a recessed opening 694. Two drain channels 695 run from the first end 691a of the body 691 to the conduit 692. Thus, the drain channels are fluidically connected to the conduit 692 and the recessed opening 694. In one embodiment (not shown), the tip 690 may comprise only one drain channel 695. Advantageously, a plurality of drain channels 695 may provide less back-pressure and, thus, a higher rate of fluid transport through the tip 690.

The body 691 may be fabricated from plastic (e.g., polypropylene, polyethylene, polytetrafluoroethylene) by molding, for example. The body 691 is shaped and dimensioned to fit in a housing (e.g., housing 510 of FIG. 5A). In any embodiment, the body 691 or the O-ring 686 can form a substantially liquid-tight seal with the walls of a housing when the body 691 is inserted into the housing. In any embodiment that includes an O-ring, 686, the O-ring 686 may function both to form a liquid-tight seal and to wipe particulate material (e.g., cell concentration agents) off the wall of the housing as the O-ring 686 is moved in relation to the wall of the housing. The shaft 651 may be coupled to the conduit 692 by means that are known in the art (e.g., by an adhesive, by press-fit). The optional O-ring 686 is disposed in a notch 689 in the body 691.

The tip 690 further comprises a filter 696. The filter 696 is coupled to the body 691. In the illustrated embodiment, the filter 696 is formed from a porous material, which can be press-fit and/or adhesively coupled to the recessed opening 694. In some embodiments, the porous material can be semi-rigid porous material (e.g., POREX filtration medium sold under the part number X6854 by Porex Corporation, Fairburn, Ga.). The filter 696 may be configured with a relatively angular or pointed end, such that the end can facilitate the penetration of a frangible seal. In alternative embodiments (not shown), the filter may comprise a membrane filter that is coupled to the body. When coupled to the body, the membrane filter is part of a fluid path that includes the conduit and a drain channel.

In some embodiments, the porosity of the filter 696 may be selected such that the filter 696 prevents only the passage of relatively large particles (e.g., >1 µm, >5 µm, or >10 µm) through it. Relatively large particles may include, for example, cell concentration agents as described herein. In these embodiments, microorganisms such as bacteria, yeast, and/or filamentous fungi (mold) may pass through the filter 696.

In some embodiments, the porosity of the filter 696 may be selected such that the filter 696 prevents only the passage of relatively small particles (e.g., <1 µm, <0.45 µm, <0.2 µm) through it. In these embodiments, microorganisms such as bacteria, yeast, and/or filamentous fungi (mold) may be retained by the filter 696.

The tip 690 further comprises a one-way valve 697 disposed in the recessed opening 694 between the filter 696 and the conduit 692. Also shown is an optional retaining washer 698 that serves to hold the one-way valve 697 in position. The one-way valve 697 may be constructed from plastic (e.g., polypropylene, polyethylene, polyester) or rubber, for example, and may be configured as a duck-bill valve, for example. In use, the one-way valve 697 substantially prevents the flow of liquid that has passed through the filter 696 from returning through the filter 696 in the opposite direction.

FIG. 6B shows a side view, partially in section of the assembled tip 690 of FIG. 6A. The one-way valve 697, optional retaining washer 698, and filter 696 are disposed in the recessed opening and are in fluidic connection with the conduit 692 and the drain channels 695. The shaft 651 is coupled to the body 691 of the tip 690.

Referring back to FIG. 5A, the detection device 500 comprising the housing 510 and plunger 550 is used in a method to detect microorganisms and, in particular, live microorganisms.

Figure 5B:
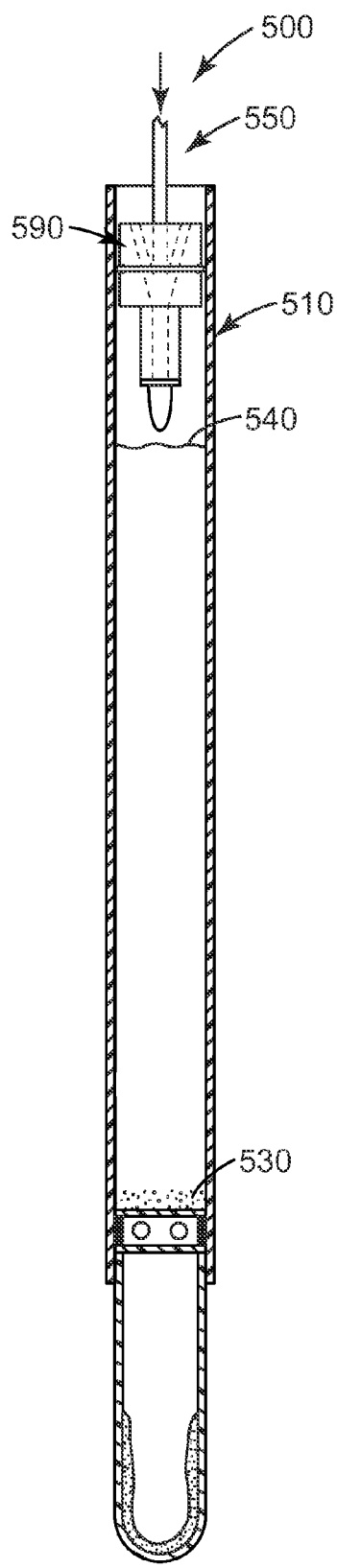
FIG. 5B-5D show a cross-sectional views of the assembled device of FIG. 5A with the plunger inserted to various depths into the housing.
Figure 5C:
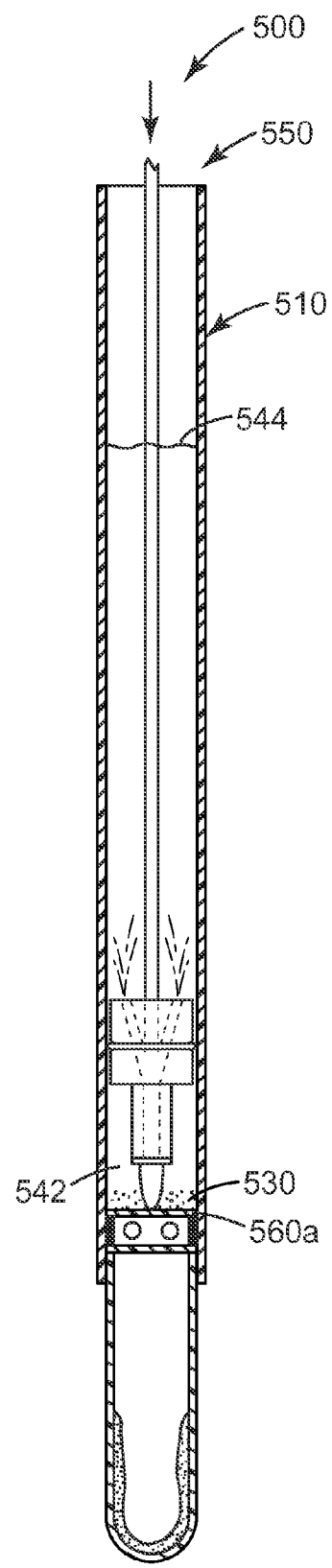

In use, a liquid sample is transferred into the upper receptacle 520 of the housing 510, where it is allowed to contact a cell concentration agent 530. After adding the liquid sample 540 to the housing 510, the tip of the plunger 550 is inserted into the housing 510 and urged (e.g., manually or mechanically) toward the lower receptacle 524 of the housing 510, as shown in FIG. 5B. As the tip 591 of the plunger 550 contacts the liquid sample 540, the liquid passes through the tip 590 and back into the housing 510, as shown in FIG. 5B. This process retains the cell concentration agent 530 and, in some embodiments, free microorganisms in a portion 542 of the liquid sample proximate the third receptacle 526.

Figure 5D:
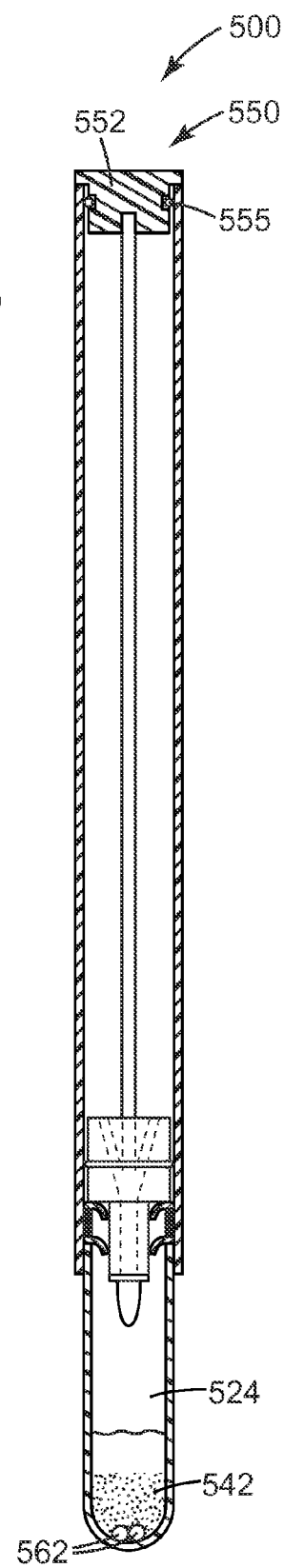

As the tip 590 of the plunger 550 penetrates the frangible seal 560a, not shown, the portion 542 of the liquid sample containing the cell concentration agent 530 contacts the hydrogel 562. Further movement of the plunger 550 (as shown in FIG. 5D) causes penetration of the frangible seal 560b, which causes the portion 542 of the liquid sample and the hydrogel 562 to transfer to the lower receptacle 524, where they contact the detection reagent 565.

Figure 7A:
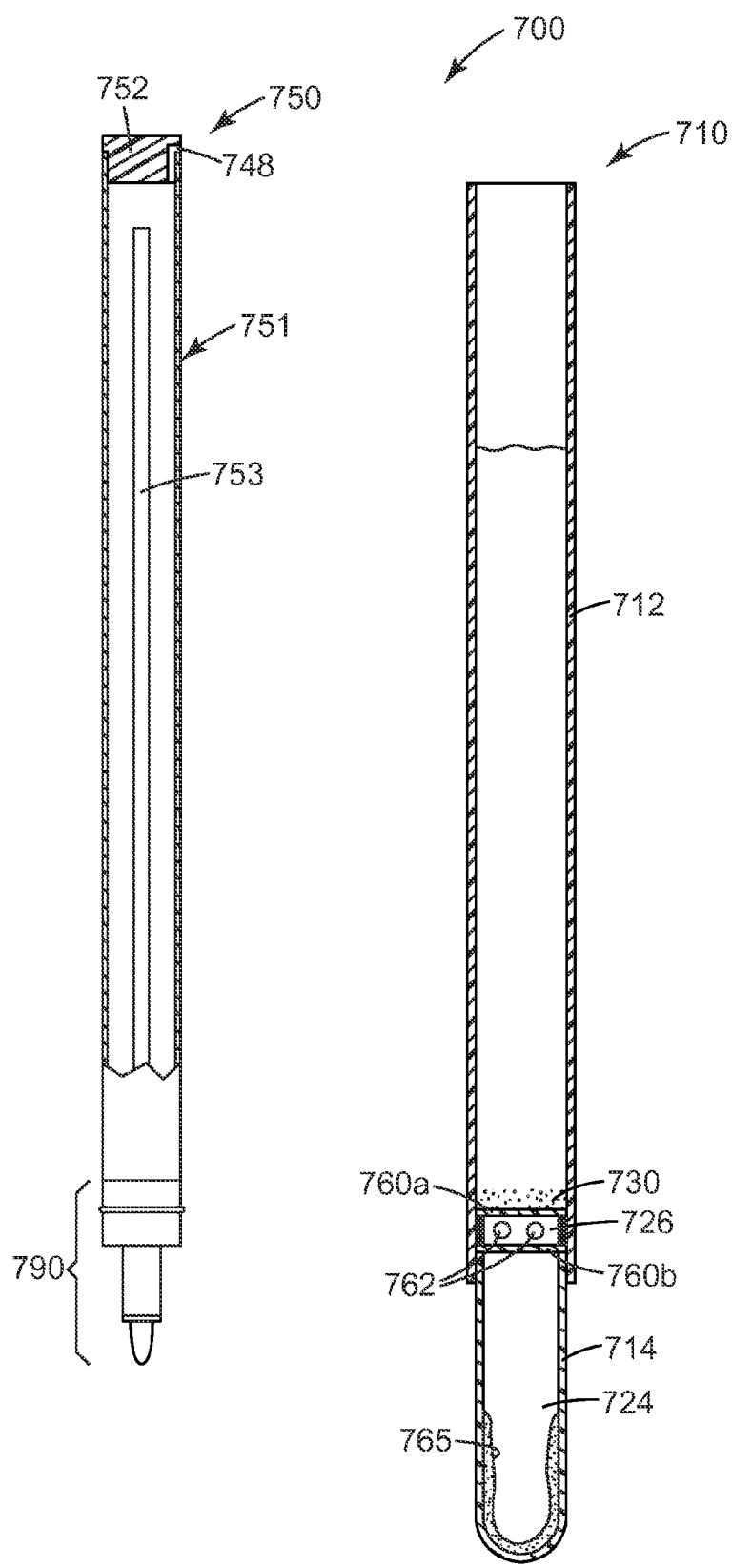
FIG. 7A shows a cross-sectional view of one embodiment of a housing and a side view of a hollow plunger, partially in section, which are both components of one embodiment of a sample preparation and detection device according to the present disclosure.

FIG. 7A shows a cross-sectional side view of another embodiment of a detection device 700 according to the present disclosure. The detection device 700 comprises a plunger 750 and a housing 610.

The housing 710 can be constructed as described above with an upper part 712 and a lower part 714. Frangible seals 760a and 760b divide the housing 710 into three receptacles, an upper receptacle 720, lower receptacle 724, and third receptacle 726. In this illustration, frangible seals 760a and 760b are located at the end of the upper receptacle 720 that is proximate the lower receptacle 724. The space between the frangible seals 760a and 760b defines a third receptacle 726. Located in the third receptacle 726 is a hydrogel 762 comprising a cell extractant. In the illustrated embodiment, the lower receptacle 724 comprises an optional detection reagent 765. An alternative construction (not shown) may have only one frangible seal 760 proximate the lower receptacle 724, with the hydrogel 762 located in the lower receptacle 724, as shown in FIG. 3C.

The plunger 750 comprises a shaft 751 coupled to a handle 752 and a tip 790. In this embodiment, the shaft 751 is hollow and the handle comprises a vent 748 to equalize the pressure between the interior and exterior of the shaft 751. The plunger further comprises an optional drain tube 753. The drain tube 753 receives liquid filtrate from the tip 790 and distributes the filtrate to the interior of the shaft 751. By functioning as an overflow valve, the drain tube 753 also reduces the volume of filtrate that can flow back through the tip 790 in the reverse direction.

Detail of the tip 790 of the plunger 750 is shown in FIG. 8.

FIG. 8A shows a partially exploded side view, partially in section, of the tip 790 of FIG. 7A. The tip 890 comprises a body 891, an optional one-way valve 897, and a filter 896. Also show in FIG. 8A is a portion of the plunger 850 comprising a hollow shaft 851 and a drain tube 853.

The body 891 includes a first end 891a, a second end 891b, and a conduit 892 running through the body 891 from the first end 891a to the second end 891b. At the first end 891a, the conduit 892 is coupled (e.g., by press-fit, and adhesive, or by a threaded connection) to the drain tube 853 of the plunger. At the second end 891b, the conduit 892 opens into a recessed opening 894. Thus, the recessed opening 894 is fluidically connected to the conduit 892 and the drain tube 853.

The body 891 may be fabricated from plastic (e.g., polypropylene, polyethylene, polytetrafluoroethylene) by molding, for example. The body 891 is shaped and dimensioned to fit in a housing (e.g., housing 710 of FIG. 7A). In any embodiment, the body 891 or the O-ring 886 can form a substantially liquid-tight seal with the walls of a housing when the body 891 is inserted into the housing. In any embodiment that includes an O-ring, 886, the O-ring 886 may function both to form a liquid-tight seal and to wipe particulate material (e.g., cell concentration agents) off the wall of the housing as the O-ring 886 is moved in relation to the wall of the housing. The shaft 851 may be coupled to the conduit 892 by means that are known in the art (e.g., by an adhesive, by press-fit). The optional O-ring 886 is disposed in a notch 889 in the body 891.

The tip 890 further comprises a filter 896. The filter 896 is coupled to the body 891 at the recessed opening 894. In the illustrated embodiment, the filter 896 is formed from a porous material, which can be press-fit and/or adhesively coupled to the recessed opening 894. In some embodiments, the porous material can be semi-rigid porous material (e.g., POREX filtration medium sold under the part number X6854 by Porex Corporation, Fairburn, Ga.). The filter 896 may be configured with a relatively angular or pointed end, such that the end can facilitate the penetration of a frangible seal. In alternative embodiments (not shown), the filter may comprise a membrane filter that is coupled to the body. When coupled to the body, the membrane filter is part of a fluid path that includes the conduit and a drain channel.

In some embodiments, the porosity of the filter 896 may be selected such that the filter 896 prevents only the passage of relatively large particles (e.g., >1 µm, >5 µm, or >10 µm) through it. Relatively large particles may include, for example, cell concentration agents as described herein. In these embodiments, microorganisms such as bacteria, yeast, and/or filamentous fungi (mold) may pass through the filter 896.

In some embodiments, the porosity of the filter 896 may be selected such that the filter 896 prevents only the passage of relatively small particles (e.g., <1 µm, <0.45 µm, <0.2 µm) through it. In these embodiments, microorganisms such as bacteria, yeast, and/or filamentous fungi (mold) may be retained by the filter 896.

The tip 890 may further comprise an optional one-way valve 897 disposed in the recessed opening 894 between the filter 896 and the conduit 892. Also shown is an optional retaining washer 898 that can serve to hold the one-way valve 897 in position. The one-way valve 897 may be constructed from plastic (e.g., polypropylene, polyethylene, polyester) or rubber, for example, and may be configured as a duck-bill valve, for example. In use, the one-way valve 897 substantially prevents the flow of liquid that has passed through the filter 896 from returning through the filter 896 in the opposite direction.

FIG. 8B shows a side view, partially in section of the assembled tip 790 of FIG. 7A. The one-way valve 897, optional retaining washer 898, and filter 896 are disposed in the recessed opening and are in fluidic connection with the conduit 892 and the drain tube 853. The shaft 851 is coupled to the body 891 of the tip 890.

Referring back to FIG. 7A, the detection device 700 comprising the housing 710 and plunger 750 is used in a method to detect microorganisms and, in particular, live microorganisms.

In use, a liquid sample is transferred into the upper receptacle 720 of the housing 710, where it is allowed to contact a cell concentration agent 730. After adding the liquid sample 740 to the housing 710, the tip 790 of the plunger 750 is inserted into the housing 710 and urged (e.g., manually or mechanically) toward the lower receptacle 724 of the housing 710, as shown in FIG. 7B. As the tip 791 of the plunger 750 contacts the liquid sample 740, the liquid passes through the tip 790, through the drain tube 753, and into the hollow shaft of the plunger 750, as shown in FIG. 7B. This process retains the cell concentration agent 730 and, in some embodiments, free microorganisms in a portion 742 of the liquid sample proximate the third receptacle 726.

As the tip 790 of the plunger 750 penetrates the frangible seal 760a, not shown, the portion 742 of the liquid sample containing the cell concentration agent 730 contacts the hydrogel 762. Further movement of the plunger 750 (as shown in FIG. 7D) causes penetration of the frangible seal 760b, which causes the portion 742 of the liquid sample and the hydrogel 762 to transfer to the lower receptacle 724, where they contact the detection reagent 765.

Figure 9:
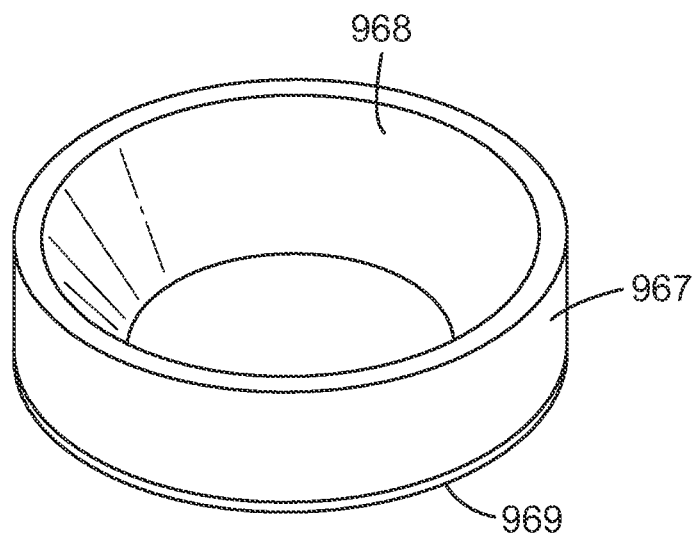
FIG. 9 shows one embodiment of a cell concentration agent collector according to the present disclosure.

Devices of the present disclosure include frangible seals in a housing. The frangible seals are pierced to transport the cell concentration agent from one compartment of the device to another compartment. In some embodiments, the amount cell concentration agent transferred in that process can be enhanced by collecting the cell concentration agent onto a relatively area of the frangible seal. FIG. 9 shows one embodiment of a collector 967 to enhance the recovery of cell concentration agent. The collector 967 is dimensioned to fit within the housing of a detection device according to the present disclosure. The collector 967 comprises a beveled edge 968 that is oriented toward the sample comprising a cell concentration agent (not shown). Typically, the beveled edge 968 faces upward such that it collects particles that are settling by the force of gravity. Alternatively, the beveled edge 968 could be oriented toward a centrifugal or a hydrodynamic force, for example, to collect particles subjected to forces other than gravity. The collector 967 further comprises an optional frangible seal 969.

The collector 967 can be fabricated from a variety of materials including, for example a polymer (e.g., polyester, polypropylene, polytetrafluoroethylene, polypropylene, polystyrene, nylon, and combinations and derivatives thereof), glass, and metal. The collector 967 may further comprise a lubricious coating to resist the adherence of particles to its surface. The beveled edge 968 may be angled (e.g. a 45-degree angle, a >45-degree angle) to facilitate the movement of particles down its slope. The frangible seal 969 is fabricated as described herein and may be coupled to the collector 967 by means that are described herein.

Figure 10A:
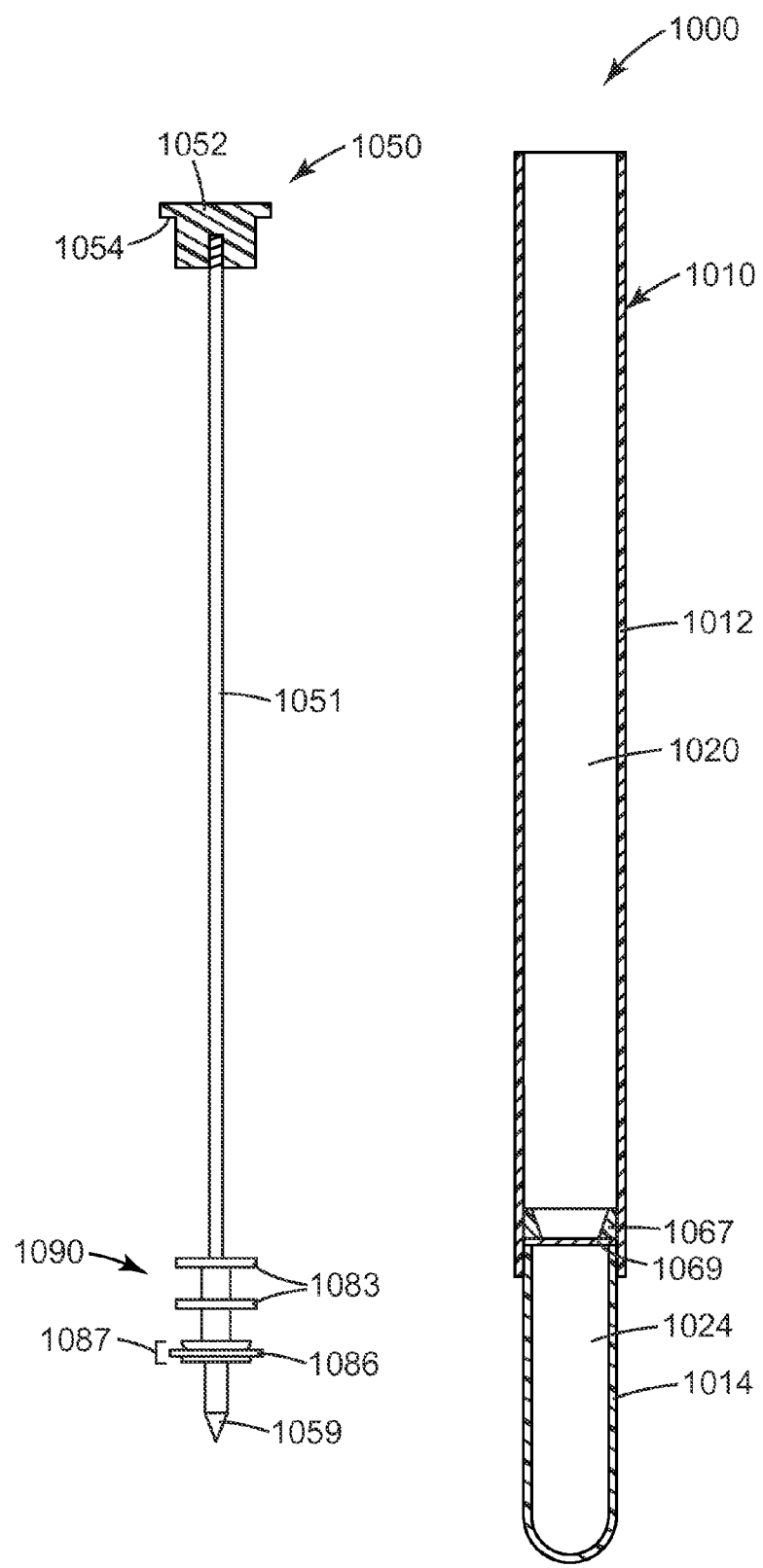
FIG. 10A shows a cross-sectional view of one embodiment of a housing and a side view of a plunger, partially in section, which are both components of one embodiment of a sample preparation and detection device according to the present disclosure.

FIG. 10A shows one embodiment of a detection device 1000 comprising a collector 1067. The device 1000 comprises a housing 1010 and a plunger 1050. The housing 1010 comprises an upper part 1012 and a lower part 1014. Disposed within the upper part 1012 and proximate the lower part 1014 is a collector 1067 with a frangible seal 1069 coupled thereto. The frangible seal 1069 is coupled to the side of the collector 1067 that is facing the lower part 1014. Thus, the frangible seal 1069 divides the housing 1010 into two isolated receptacles, an upper receptacle 1020 and a lower receptacle 1024.

The plunger 1050 comprises a handle 1052, a shaft 1051, and a tip 1090. The handle 1052 can be constructed as described above and may comprise an optional rim 1054 that engages the housing 1010 to prevent the plunger 1050 from being inserted too far into the housing 1010. The handle 1052 can be coupled to the shaft 1051 via a threaded fit or by other coupling means (e.g., press-fit, adhesive). The tip 1090 may be fabricated fusing processes and materials described for other tip embodiments described herein. The tip 1090 may comprise one or more guides 1083. The guides are dimensioned to loosely fit within the interior of the housing 1010 and function to reduce lateral movement of the tip 1090 as the tip 1090 moves longitudinally through the housing 1010.

The tip 1090 further comprises a scraper 1086, which is held in a fixed position on the tip 1090. In the illustrated embodiment, the scraper 1086 is held in a fixed position by retaining member 1087. The retaining member 1087 can be molded or machined as part of the tip 1090 or it can comprise a bracket or plurality of brackets coupled to the tip 1090. Alternatively, the scraper 1086 may be directly coupled (e.g., adhesively coupled) to the tip 1090.

The scraper 1086 is disc-shaped and is dimensioned to form a relatively tight fit inside the housing 1010. In some embodiments, the scraper can comprise an-O-ring. The scraper 1086 should substantially maintain its shape when immersed in an aqueous liquid. Although the scraper should be dimensioned to form a relatively tight fit inside the housing, the scraper should be relatively flexible to permit fluid to flow around its edge as the plunger is pushed through a liquid sample in the housing 1010. Suitable materials for fabricating the scraper 1086 include, for example polyurethane rubber.

Figure 10B:
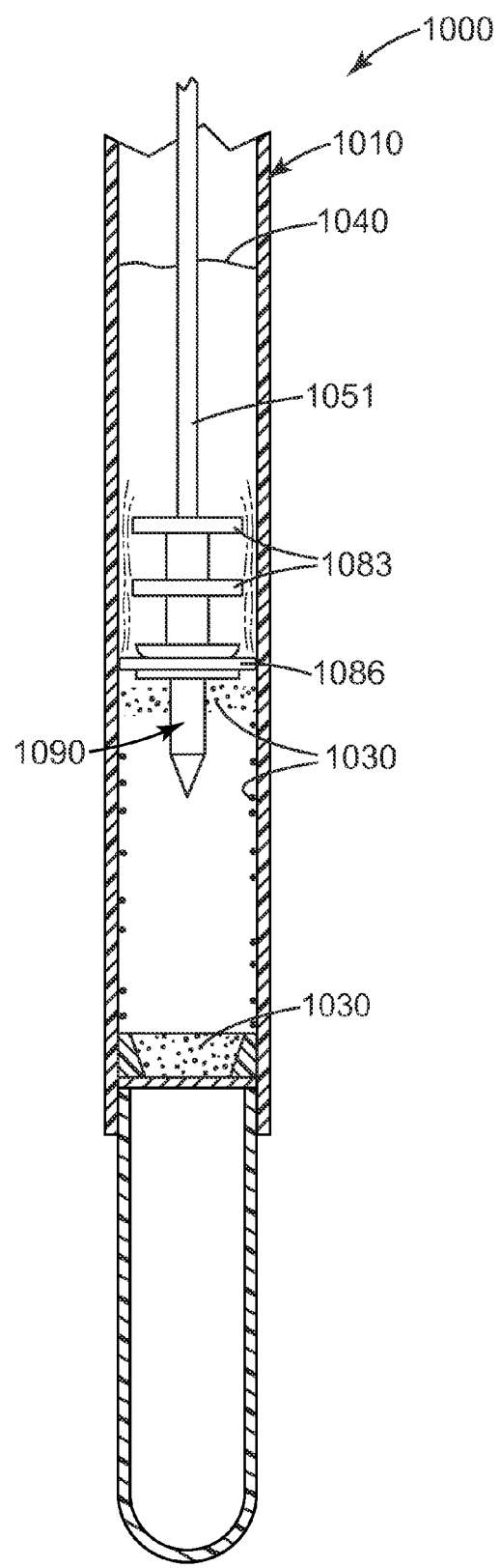
FIG. 10B shows a side view, partially in section, of the assembled device of FIG. 10A.

In use, a liquid sample 1040 and a cell concentration agent 1030 are contacted in the housing 1010 of the device, as shown in FIG. 10B. The plunger 1050 is inserted into the housing 1010 and the tip 1090 of the plunger 1050 is urged toward the bottom of the housing 1010. As the tip 1090 passes through the liquid sample 1040, the cell concentration agent 1030 is urged toward the bottom of the housing 1010 by the scraper 1086, while the liquid sample 1040 flows around the edge of the scraper 1086. Advantageously, this devices allows the user to collect and concentrate the cell concentration agent 1030 in a substantially shorter period of time than possible if the cell concentration agent 1030 is allowed to settle by gravity force to the bottom of the housing 1010. Furthermore, the flexible scraper facilitates collecting a portion of cell concentration agent 1030 that might otherwise adhere to the walls of the housing. Thus, the inventive device 1000 increases the recovery of the cell concentration agent and, thereby, increases the sensitivity of a method that uses a cell concentration agent to concentrate microorganisms.

It should be recognized that, in a sample preparation and detection device in which the cell concentration agent comprises ferromagnetic materials (e.g., particles), that a magnet or an electromagnet can be positioned adjacent the device to draw the particles (and microorganisms coupled thereto) to a desired location for collecting the particles and/or transferring them to another receptacle. In some embodiments, the magnet can be positioned adjacent the device (e.g., adjacent the bottom of the device) after a sufficient period of time to allow for the cell concentration agent to couple substantially all of the microorganisms in the liquid sample.

Methods of Detecting Biological Analytes from Live Cells:

Methods of the present disclosure include methods for the detection of biological analytes that are released from live cells including, for example, live microorganisms, after exposure to an effective amount of cell extractant.

Methods of the present disclosure include the formation of a liquid mixture comprising a sample suspected of containing live cells and a hydrogel comprising a cell extractant. Methods of the present disclosure further include detecting a biological analyte. Detecting a biological analyte can further comprise quantitating the amount of biological analyte in the sample.

In one aspect, the present disclosure provides a method of detecting cells in a sample. The method comprises providing a cell concentration agent, a hydrogel comprising a cell extractant and a liquid sample suspected of containing cells. Suitable cell concentration agents are described in International Publication No. WO2009/085357, which is incorporated herein by reference in its entirety.

The method further comprises contacting the liquid sample and the cell concentration agent for a period of time. The cell concentration agent can comprise particles, fibers, a matrix (e.g., a fibrous matrix) comprising particles, or any combination of two or more of the foregoing. The cell concentration agent can be suspended in the liquid sample during the contact period. The suspension can be placed into a vessel, such as a tube, a flask, a beaker, or any of the detection devices described herein. In certain preferred embodiments, the liquid sample is mixed with the cell concentration agent for a period of time by, for example, stirring, vortexing, or vibrating the suspension. While the cell concentration agent is contacted with the liquid sample, cells from the liquid sample are coupled to the cell concentration agent.

The method further comprises isolating the cell concentration agent from at least a portion of the liquid sample. During this process, the cell concentration agent may be concentrated in a smaller volume than the original liquid sample. The cell concentration agent can be isolated from at least a portion of the liquid sample by a variety of means. For example, if the cell concentration agent has a higher specific gravity than the liquid sample, the cell concentration agent can settle to the bottom of the suspension. At least a portion of the liquid sample can be removed (e.g., by pipetting or decanting). Alternatively, or additionally, at least a portion of the liquid sample can be removed by centrifugation or filtration.

A filter can be described by its pore size (for example by its bubble point pore size). The bubble point pore size of a filter is generally the average of the largest size of the pores of the filter. In some embodiments, the filter can have an average pore size that is less than the average size of the cell concentration agent. The ability to utilize filters having these relatively large pore sizes offers significant advantages to methods as disclosed herein when compared with other methods for separating microorganisms from samples, such as water samples.

In an embodiment, the filter can have an average pore size that is at least about 1 micrometer ($\mu$m) or larger. In an embodiment, the filter can have an average pore size that is at least about 1.5 $\mu$m or larger. In an embodiment, the filter can have an average pore size that is at least about 5 $\mu$m or larger. In an embodiment, the filter can have an average pore size that is at least about 10 $\mu$m or larger. As larger pore size filters are utilized, the sample will be easier and quicker to filter as the back pressure decreases with increase in pore size.

Filtering the sample can be accomplished using known methods. In an embodiment, the method of filtering that is chosen can be dictated at least in part on the particular application of the method. For example, the sample can be filtered using a negative vacuum, by applying a positive pressure, by the force of gravity. The particular technique used to filter the sample can depend at least in part on the type of device that is being utilized to carry out the method. For example, in order to utilize a negative vacuum, the device can be configured with a port that can be or reversibly attached to a source of vacuum; and in order to apply a positive pressure, the device can be configured to allow a user to apply a positive pressure by applying a force with their hands. In an embodiment, the sample can be filtered by applying a positive pressure. Filtering using positive pressure (or using the force of gravity) can offer the advantage of easily being able to carry out the method in the field without the need for any further equipment, such as a vacuum pump.

In some embodiments, a centrifugation step may include the use of a relatively low-speed centrifugation in which the cell concentration agents separate (e.g., by sedimentation) out of the liquid but microorganisms (e.g., bacteria, yeast molds, spore) that are not bound to the cell concentration agent remain suspended in the liquid.

Optionally, the cell concentration agent can be resuspended in a wash solution (e.g., water or a buffer solution) and the cell concentration agent can be isolated from at least a portion of the wash solution. It will be recognized that a washing step can function to remove from the liquid sample contaminating materials that may interfere with a growth and/or detection process.

The method further comprises forming a liquid mixture comprising the isolated cell concentration agent and the hydrogel, wherein the cell extractant is released from the hydrogel. In some embodiments, when the cell concentration agent is isolated from at least a portion of the liquid sample, the cell concentration agent remains in a residual volume of liquid. Additional liquid (e.g., water or a buffer solution) optionally can be added to the cell concentration agent. In the embodiments wherein the cell concentration agent is filtered out of the liquid sample, the cell concentration agent can be resuspended in a volume of liquid (e.g., water or a buffer solution). The liquid suspension comprising the cell concentration agent is contacted with the hydrogel, thereby releasing the cell extractant into the liquid mixture. In methods involving the use of filters to collect the cell concentration agent, the liquid suspension comprising the cell concentration agent can also comprise the filter. An effective amount of cell extractant can be released from the hydrogel to effect the release of biological analytes from cells, if present, in the mixture. The release of an effective amount of cell extractant can occur over a period of time (e.g., up to several seconds, up to several minutes, up to an hour, or longer).

The method further comprises detecting an analyte. The detection of the biological analytes can involve the use of a detection system. Detection systems for certain biological analytes such as a nucleotide (e.g., ATP, NADH, NAD), a polynucleotide (e.g., DNA or RNA) or an enzyme (e.g., NADH dehydrogenase or adenylate kinase) are known in the art and can be used according to the present disclosure. Methods of the present disclosure include known detections systems for detecting a biological analyte. Preferably, the accuracy and sensitivity of the detection system is not significantly reduced by the cell extractant. More preferably, the detection system comprises a homogeneous assay.

In some embodiments, detecting the biological analyte can comprise detecting the analyte directly in a vessel (e.g., a tube, a multi-well plate, and the detection devices described herein) in which the liquid mixture comprising the sample and the hydrogel comprising a cell extractant is formed. In some embodiments, detecting the biological analyte can comprise transferring at least a portion of the liquid mixture to a container other than the vessel in which the liquid mixture comprising the sample and the hydrogel comprising a cell extractant is formed. In some embodiments, detecting the biological analyte may comprise one or more sample preparation processes, such as pH adjustment, dilution, filtration, centrifugation, extraction, and the like.

In some embodiments, the detection system comprises a detection reagent. Detection reagents include, for example, dyes, enzymes, enzyme substrates, binding partners (e.g., an antibody, a monoclonal antibody, a lectin, a receptor), labeled binding partners, and/or cofactors. In some embodiments, the detection reagent comprises a hydrogel, such as the hydrogels comprising an enzyme or enzyme substrate, as described in International Publication No. WO2010/039627. In some embodiments, the detection system comprises an instrument. Nonlimiting examples of detection instruments include a spectrophotometer, a luminometer, a plate reader, a thermocycler, an incubator.

Detection systems can include detection instruments. Detection instruments are known in the art and can be used to detect biological analytes colorimetrically (i.e., by the absorbance and/or scattering of light), fluorescently, or lumimetrically. Examples of the detection of biomolecules by luminescence are described by F. Gorus and E. Schram (Applications of bio- and chemiluminescence in the clinical laboratory, 1979, Clin. Chem. 25:512-519).

An example of a biological analyte detection system is an ATP detection system. The ATP detection system can comprise an enzyme (e.g., luciferase) and an enzyme substrate (e.g., luciferin). The ATP detection system can further comprise a luminometer. In some embodiments, the luminometer can comprise a bench top luminometer such as, for example, the FB-12 single tube luminometer (Berthold Detection Systems USA, Oak Ridge, Tenn.). In some embodiments, the luminometer can comprise a handheld luminometer such as, for example, the NG Luminometer, UNG2 (3M Company, St. Paul, Minn.).

In some embodiments, the biological analyte is detected at a single time point. In some embodiments, the biological analyte is detected at two or more time points. When the biological analyte is detected at two or more time points, the amount of biological analyte detected at a first time (e.g., before an effective amount of cell extractant is released from a hydrogel to effect the release of biological analytes from live cells in at least a portion of the sample) point can be compared to the amount of biological analyte detected at a second time point (e.g., after an effective amount of cell extractant is released from a hydrogel to effect the release of biological analytes from live cells in at least a portion of the sample). In some embodiments, the measurement of the biological analyte at one or more time points is performed by an instrument with a processor. In certain preferred embodiments, comparing the amount of biological analyte at a first time point with the amount of biological analyte at a second time point is performed by the processor.

For example, the operator measures the amount of biological analyte in the sample after the liquid mixture including the sample and the hydrogel comprising a cell extractant is formed. The amount of biological analyte in this first measurement ($T_1$) can indicate the presence of "free" (i.e. acellular) biological analyte and/or biological analyte from non-viable cells in the sample. In some embodiments, the first measurement can be made immediately (e.g., about 1 second) after the liquid mixture including the sample and the hydrogel comprising a cell extractant is formed. In some embodiments, the first measurement can be at least about 5 seconds, at least about 10 seconds, at least about 20 seconds, at least about 30 seconds, at least about 40 seconds, at least about 60 seconds, at least about 80 seconds, at least about 100 seconds, at least about 120 seconds, at least about 150 seconds, at least about 180 seconds, at least about 240 seconds, at least about 5 minutes, at least about 10 minutes, at least about 20 minutes after the liquid mixture including the sample and the hydrogel comprising a cell extractant is formed. These times are exemplary and include only the time up to that the detection of a biological analyte is initiated. Initiating the detection of a biological analyte may include diluting the sample and/or adding a reagent to inhibit the activity of the cell extractant. It will be recognized that certain detection systems (e.g., nucleic acid amplification or ELISA) can generally take several minutes to several hours to complete.

The operator allows the sample to contact the hydrogel comprising the cell extractant for a period of time after the first measurement of biological analyte has been made. After the sample has contacted the hydrogel for a period of time, a second measurement of the biological analyte is made. In some embodiments, the second measurement can be made up to about 0.5 seconds, up to about 1 second, up to about 5 seconds, up to about 10 seconds, up to about 20 seconds, up to about 30 seconds, up to about 40 seconds, up to about 60 seconds, up to about 90 seconds, up to about 120 seconds, up to about 180 seconds, about 300 seconds, at least about 10 minutes, at least about 20 minutes, at least about 60 minutes or longer after the first measurement of the biological analyte. These times are exemplary and include only the interval of time from which the first measurement for detecting the biological analyte is initiated and the time at which the second measurement for detecting the biological analyte is initiated. Initiating the detection of a biological analyte may include diluting the sample and/or adding a reagent to inhibit the activity of the cell extractant.

Preferably, the first measurement of a biological analyte is made about 1 second to about 240 seconds after the liquid mixture including the sample and the hydrogel comprising a cell extractant is formed and the second measurement, which is made after the first measurement, is made about 1.5 seconds to about 540 seconds after the liquid mixture is formed. More preferably, the first measurement of a biological analyte is made about 1 second to about 180 seconds after the liquid mixture is formed and the second measurement, which is made after the first measurement, is made about 1.5 seconds to about 120 seconds after the liquid mixture is formed. Most preferably, the first measurement of a biological analyte is made about 1 second to about 5 seconds after the liquid mixture is formed and the second measurement, which is made after the first measurement, is made about 1.5 seconds to about 10 seconds after the liquid mixture is formed.

The operator compares the amount of a biological analyte detected in the first measurement to the amount of biological analyte detected in the second measurement. An increase in the amount of biological analyte detected in the second measurement is indicative of the presence of one or more live cells in the sample.

In certain methods, it may be desirable to detect the presence of live somatic cells (e.g., nonmicrobial cells). In these embodiments, the hydrogel comprises a cell extractant that selectively releases biological analytes from somatic cells. Nonlimiting examples of somatic cell extractants include nonionic detergents, such as non-ionic ethoxylated alkylphenols, including but not limited to the ethoxylated octylphenol Triton X-100 (TX-100) and other ethoxylated alkylphenols; betaine detergents, such as carboxypropylbetaine (CB-18), NP-40, TWEEN, Tergitol, Igepal, commercially available M-NRS (Celsis, Chicago, Ill.), M-PER (Pierce, Rockford, Ill.), CellLytic M (Sigma Aldrich). Cell extractants are preferably chosen not to inactivate the analyte and its detection reagents.

In certain methods, it may be desirable to detect the presence of live microbial cells. In these embodiments, the hydrogel can comprise a cell extractant that selectively releases biological analytes from microbial cells. Nonlimiting examples of microbial cell extractants include quaternary ammonium compounds, including benzalkonium chloride, benzethonium chloride, 'cetrimide' (a mixture of dodecyl-, tetradecyl- and hexadecyl-trimethylammonium bromide), cetylpyridium chloride; amines, such as triethylamine (TEA) and triethanolamine (TeolA); bis-Biguanides, including chlorhexidine, alexidine and polyhexamethylene biguanide dialkyl ammonium salts, including N-(n-dodecyl)-diethanolamine, antibiotics, such as polymyxin B (e.g., polymyxin B1 and polymyxin B2), polymyxin-beta-nonapeptide (PMBN); alkylglucoside or alkylthioglucoside, such as Octyl-β-D-1-thioglucopyranoside (see U.S. Pat. No. 6,174,704 herein incorporated by reference in its entirety); nonionic detergents, such as non-ionic ethoxylated alkylphenols, including but not limited to the ethoxylated octylphenol Triton X-100 (TX-100) and other ethoxylated alkylphenols; betaine detergents, such as carboxypropylbetaine (CB-18); and cationic, antibacterial, pore forming, membrane-active, and/or cell wall-active polymers, such as polylysine, nisin, magainin, melittin, phospholipase $A_2$, phospholipase $A_2$ activating peptide (PLAP); bacteriophage; and the like. See e.g., Morbe et al., Microbiol. Res. (1997) vol. 152, pp. 385-394, and U.S. Pat. No. 4,303,752 disclosing ionic surface active compounds which are incorporated herein by reference in their entirety.

Cell extractants are preferably chosen not to inactivate the biological analyte and/or a detection reagent used to detect the biological analyte.

In certain alternative methods to detect the presence of live microbial cells in a sample, the sample can be pretreated with a somatic cell extractant for a period of time (e.g., the sample is contacted with a somatic cell extractant for a sufficient period of time to extract somatic cells before a liquid mixture including the sample and a hydrogel comprising a microbial cell extractant is formed). In the alternative embodiment, the amount of biological analyte detected at the first measurement will include any biological analyte that was released by the somatic cells and the amount of additional biological analyte, if any, detected in the second measurement will include biological analyte from live microbial cells in the sample.

Methods to detect the presence of a microorganism in a sample can include the use of the detection devices disclosed herein. In certain embodiments, the method comprises providing i) a sample suspected of containing cells, ii) a detection article comprising a housing with two or more receptacles and an opening configured to receive the sample, iii) a cell concentration agent, and iv) a means for isolating and transferring the cell concentration agent from a upper receptacle to a lower receptacle in the housing, and v) a hydrogel comprising a cell extractant. In these embodiments, the detection device can comprise any one of the detection devices 100, 200, 300, or 400, shown in FIGS. 1-4. Optionally, the detection device can comprise the cell concentration agent and/or the hydrogel.

The method further comprises transferring the sample into an upper receptacle in the housing wherein, in a liquid medium, the sample material is contacted with the cell concentration agent. The sample can comprise liquids, solids, semi-solids, or combinations thereof, which are transferred into the upper receptacle of the housing. If the sample does not comprise a liquid medium, a liquid medium (e.g., water or a buffered solution) can be added to the upper receptacle. A cell concentration agent is added to the liquid sample. The cell concentration agent is allowed to contact the liquid sample for a period of time. Optionally, the mixture can be mixed during the contact period by, for example, shaking, stirring, vortexing, and/or vibrating the housing. Preferably, the housing is closed (e.g., with optional cap) during the contact period to avoid loss of the sample and/or cell concentration agent.

The method further comprises isolating, from at least a portion of the liquid medium, the cell concentration agent, wherein isolating the cell concentration agent comprises transferring the cell concentration agent to a lower receptacle in the housing. As described herein, there are a variety of means for isolating the cell concentration agent. Non-limiting examples of means to isolate and transfer the cell concentration agent include partitioning and transferring the cell concentration agent through a passageway using a plunger (see FIGS. 1 and 2), collecting and transferring the cell concentration agent in the cavity of a one-way valve (see FIG. 3), and concentrating and transferring the cell concentration agent using a drain valve and a plunger (see FIG. 4).

The method further comprises forming a liquid mixture comprising the isolated cell concentration agent and the hydrogel, wherein the cell extractant is released into the mixture. The liquid mixture comprising the cell concentration agent is contacted with a hydrogel comprising a cell extractant. The hydrogel (e.g., a hydrogel bead) can be contacted with the liquid mixture in the upper receptacle and/or lower receptacle of the housing. In some embodiments, the lower receptacle of the housing contains the hydrogel (see FIGS. 1 and 3) and the liquid mixture is contacted with the hydrogel when the mixture is transferred into the lower receptacle. In some embodiments, the hydrogel is disposed in a third receptacle (see FIGS. 2 and 4), through which the liquid sample passes (thereby contacting the liquid sample with the hydrogel) as the liquid sample is transferred from the upper receptacle to the lower receptacle.

It is recognized that, although FIGS. 2 and 4 show the use of a plunger to pierce the frangible seals and transfer the cell concentration agent to the lower receptacle, alternative instruments (e.g., a swab, a pipette, a filter) could be used instead of a plunger. In a method where such alternative instruments are used, it is preferable to remove at least a portion of the liquid sample (e.g., by decanting, pipetting, filtering, or by opening the drain valve, if present) such that the entire liquid sample is not transferred to the second receptacle when the frangible seal is pierced by the alternative instrument.

The method further comprises detecting a biological analyte. The biological analyte can be detected, as described herein, in the lower receptacle of the detection device before an effective amount of cell extractant is released from the hydrogel into the liquid mixture comprising the cell concentration agent. The biological analyte can be detected, as described herein, in the lower receptacle of the detection device after an effective amount of cell extractant is released from the hydrogel into the liquid mixture comprising the cell concentration agent. The biological analyte can be detected, as described herein, in the lower receptacle of the detection device before and after an effective amount of cell extractant is released from the hydrogel into the liquid mixture comprising the cell concentration agent.

It is anticipated that any of the methods disclosed herein can further comprise a biological growth step. The growth step is facilitated by providing a nutrient medium to support the growth of a microorganism. The nutrient medium can be mixed with the sample before, during, or after the concentration of microorganisms by the cell concentration agent. In some embodiments, the biological growth step occurs after the microorganisms have been concentrated by the cell concentration agent but before the biological analyte is detected. In some embodiments, the nutrient medium can contain nutrients and/or selective agents (e.g., salts, antibiotics) that favor the growth of certain types of microorganisms over other microorganisms that may be present in the sample.

Method of Concentrating a Particulate Cell Concentration Agent:

The present disclosure provides devices for concentrating a particulate cell concentration agent. The method includes providing a device to separate a portion of a liquid sample from a suspension the particulate material in the liquid sample. Suitable devices include, for example, the devices shown and described in FIG. 2A, FIG. 3A, FIG. 4A, FIG. 5A, FIG. 7A, and FIG. 10A. The devices each comprise a housing to contain a liquid sample including a particulate cell concentration agent and a means for separating the particulate cell concentration agent from at least a portion of the liquid sample.

In FIG. 2A, the means for separating the particulate cell concentration agent includes the taper region 218 and the plunger comprising a lower seal 256. In FIG. 3A, the means for separating the particulate cell concentration agent includes the dead-end valve 370 and valve actuator 372. In FIG. 4A, the means for separating the particulate cell concentration agent includes the drain valve 480 and valve gate 482. In FIGS. 5A and 7A, the means for separating the particulate cell concentration agent includes the plunger comprising fluid path with a filter 596 disposed in the fluid path. In FIG.

10A, the means for separating the particulate cell concentration agent includes the plunger with a scraper that is configured to permit the passage of liquid between the edge of the scraper and the housing.

The method further comprises forming a suspension of particulate cell concentration agent in a liquid sample. The suspension may be formed in the housing or it may be formed outside the housing. If the suspension is formed outside of the housing, the method further comprises transferring the suspension into the housing. The method further comprises contacting the particulate cell concentration agent with the liquid sample for a period of time sufficient to capture a microorganism. The contacting may occur in the housing. The contacting may occur outside the housing. The contacting may occur both outside and inside the housing. The method further comprises separating a portion of a liquid sample from a suspension the particulate material in the liquid sample, as described above for the devices of FIGS. 2A, 3A, 4A, 5A, 7A, and 10A.

Sample Preparation and Detection Kits:

Components and/or devices of the present disclosure can be packaged together with instructions and optionally, accessory articles or reagents, to produce sample preparation and detection kits. Thus, in one aspect, the present disclosure provides a kit comprising i) a housing comprising at least two receptacles with a passageway therebetween, ii) means for isolating a upper receptacle from a lower receptacle in the housing, iii) a cell concentration agent, and iv) means for transferring the cell concentration agent from the upper receptacle to the lower receptacle. The upper receptacle comprises an opening configured to receive a sample. The lower receptacle comprises a detection reagent disposed therein. In some embodiments, the housing can further comprise the means for isolating the upper receptacle from the lower receptacle, as described herein. In some embodiments, the housing can further comprise the means for transferring the cell concentration agent from the upper receptacle to the lower receptacle. In some embodiments, the cell concentration agent is disposed in the upper receptacle of the housing.

In some embodiments, kits of the present disclosure include accessory articles or reagents that can be used with the sample preparation and detection devices. Nonlimiting examples of accessory articles include a sample acquisition device, a filter, a glove, a culture device (e.g., a petri plate, a culture tube, a PETRIFILM plate obtained from 3M Company (St. Paul, Minn.), or the like), nucleic acid isolation or amplification reagents, immunoassay devices such as lateral flow devices, ELISA plates and reagents, or any combination of two or more of the foregoing articles. Nonlimiting examples of accessory reagents include water, a buffering agent, an indicator (e.g., a pH indicator), a dye, a somatic cell extractant, a hydrogel comprising a cell extractant, a binding partner as described herein, an enzyme, an enzyme substrate, oligonucleotides, control samples or any combination of two or more of the foregoing reagents.

EXAMPLES

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

Materials:

All bacterial cultures were obtained from The American Type Culture Collection (ATCC, Manassas, Va.), unless specified otherwise.

All water was obtained as 18 megaohm sterile deionized water using a Milli-Q™ Gradient deionization system from Millipore Corporation (Bedford, Mass.), unless specified otherwise.

CM-111: amorphous, spheroidized magnesium silicate; microspheres were obtained as 3M™ Cosmetic Microspheres CM-111 from 3M Company, St. Paul, Minn. The particles were shaped as solid spheres with particle density of 2.3 g/cc and had a surface area approximately 3.3 $m^2/g$. Ninety percent of the particles were less than about 11 microns. Fifty percent of the particles were less than about 5 microns. Ten percent of the particles were less than about 2 microns. CM-111 microspheres were prepared as described in Example 1 of International Publication No. WO2011/079038, which is incorporated herein by reference in its entirety.

The 100× adsorption buffer containing 500 mM KCl, 100 mM $CaCl_2$, 10 mM $MgCl_2$, and 100 mM $K_2HPO_4$ at pH 7.2 was prepared and filter-sterilized prior to use.

Surface-sterilized components were contacted (wiped with or immersed in) 70% isopropyl alcohol. The excess alcohol was poured off and the components were allowed to air-dry for at least 30 minutes before use.

All chemicals were obtained from Sigma-Aldrich Chemical Company, Milwaukee, Wis., unless specified otherwise.

Example 1

Incorporation of Cell Extractant into Hydrogel Beads after Polymerization of the Hydrogel Hydrogel beads were prepared as described in example 1 of the International Patent Publication No. WO 2007/146722. Active beads were prepared by drying as described in example 19 and then soaking in active solution as described in example 23 of the International Patent Publication No. WO 2007/146722. One gram of beads was dried at 60° C. for 2 h to remove water from the beads. The dried beads were soaked in 2 grams of 50% (w/v) aqueous solutions of BARDAC 205M (Lonza Group Ltd., Valais, Switzerland) for at least 3 hrs to overnight at room temperature. After soaking, the beads were poured into a Buchner funnel to drain the beads and then rinsed with 10 to 20 ml of distilled water. The excess water was removed from the surface of the beads by blotting them with a paper towel. The beads were stored in a jar at room temperature for at least two weeks before they were used.

Example 2

Cell Concentration by Use of Microparticles and Detection Using Cell Extractant-Loaded Hydrogels and ATP Bioluminescence 3M™ CLEAN-TRACE Surface ATP system was obtained from 3M Company (St. Paul, Minn.). Pure cultures of *E. coli* ATCC 51183 were inoculated into tryptic soy broth and grown overnight at 37° C. The bacterial culture was diluted to approximately $10^6$ or $10^5$ CFU/ml in Butterfield's buffer (pH 7.2±0.2; monobasic potassium phosphate buffer solution; VWR, West Chester, Pa.) and 100 microliters of the diluted suspension were added directly to individual tubes containing ten ml of deionized water (Milli-Q Biocel System, Millipore, Mass.) samples to obtain approximately $10^5$ CFU or $10^4$ CFU in ten ml, respectively. Ten mg of autoclaved CM-111 3M™

Cosmetic Microspheres (calcined amorphous spheroidized magnesium silicate powders; 3M Company; St. Paul, Minn.) were added to the tubes containing cells and mixed at room temperature for about 15 min. The particles were allowed to settle and the supernatant was removed. The particles were suspended in 100 µl of Butterfield's buffer and transferred to 1.5 ml microfuge tubes. Four hundred microliters of luciferase/luciferin liquid reagent solution from CLEAN-TRACE surface ATP system was added to the tubes. For the control (unconcentrated) reactions, 100 µl of approximately $10^6$ or $10^5$ CFU/ml cell suspension were added to 1.5 ml microfuge tubes and 400 µl of luciferase/luciferin liquid reagent solution from Clean-Trace surface ATP system was added to the tubes. Immediately after adding the reagent, hydrogel beads (about 11 mg) containing a cell extractant were added to individual tubes and relative light units (RLUs) measurements were recorded at 10 sec intervals in a benchtop luminometer (20/20n single tube luminometer from Turner Biosystems, Sunnyvale, Calif.). Luminescence measurements were obtained from the luminometer using 20/20n SIS software that was provided with the luminometer. The light signal was integrated for 1 second and the results, expressed in RLU, are presented in Table 1.

The data indicate that, using the protocol described herein, the microparticles were able to concentrate the microbial cells and the cell extractant released from the hydrogel beads was able to extract ATP from *E. coli*. The results further indicate that ATP released from the cells reacted with the ATP-detection reagents, which resulted in measurable bioluminescence.

TABLE 1

Detection of ATP from *E. coli* cells coupled to a cell concentration agent and exposed to microbial cell extractants released from a hydrogel. Values expressed in the table are relative light units (RLUs).

| Time | Unconcentrated | | Concentrated | |
| --- | --- | --- | --- | --- |
| (sec) | $10^4$ Cfu | $10^5$ Cfu | $10^4$ Cfu | $10^5$ Cfu |
| 10 | 1226 | 2552 | 904 | 1648 |
| 20 | 1239 | 2648 | 948 | 1735 |
| 30 | 1265 | 2681 | 1000 | 1735 |
| 40 | 1272 | 2820 | 1067 | 1786 |
| 50 | 1280 | 3152 | 1107 | 1818 |
| 60 | 1312 | 3914 | 1147 | 1948 |
| 70 | 1352 | 4960 | 1178 | 2139 |
| 80 | 1393 | 6391 | 1197 | 2388 |
| 90 | 1440 | 8258 | 1226 | 2732 |
| 100 | 1538 | 10230 | 1250 | 3188 |
| 120 | 1618 | 11859 | 1260 | 3820 |
| 130 | 1704 | 12969 | 1286 | 4681 |
| 140 | 1838 | 13527 | 1297 | 5842 |
| 150 | 1905 | 13759 | 1318 | 6721 |
| 160 | 2006 | 13735 | 1309 | 6675 |
| 170 | 2088 | 13762 | 1314 | 6513 |
| 180 | 2119 | 13537 | 1330 | 6428 |
| 190 | 2169 | 13426 | 1363 | 6321 |
| 200 | 2140 | 13353 | 1375 | 6220 |
| 210 | 2141 | 13128 | 1342 | 6196 |
| 220 | 2143 | 13014 | 1389 | 6142 |
| 230 | 2155 | 12903 | 1381 | 6076 |
| 240 | 2110 | 12780 | 1401 | 6023 |

Example 3

Detection of Microbial Cells in a Unitary Sample Preparation and Detection Device Using an ATP Bioluminescence Detection System A unitary sample preparation and detection device 200, as shown in FIG. 2, is used in this Example. The device contains approximately 10 mg of autoclaved CM-111 3M Cosmetic Microspheres in the upper receptacle 220. Lower receptacle 224 contains a liquid detection reagent 265, which consists of approximately 0.6 milliliters of the luciferase/luciferin liquid reagent solution from a CLEAN-TRACE surface ATP system. The third receptacle 226 contains two BARDAC 205M beads made according to Preparative Example 5 of International Publication No. WO2010/039627. Ten milliliters of sterile deionized water is added to the upper receptacle 220 of the unitary devices 200 immediately before use.

*E. coli* overnight cultures are prepared as described in Example 2. The bacterial culture is diluted to approximately $10^6$ or $10^5$ CFU/ml in Butterfield's buffer. One hundred microliters of the diluted suspension are pipetted directly into upper receptacle 220 of the unitary devices 200 to obtain a suspension of approximately $10^5$ CFU or $10^4$ CFU in ten milliliters, respectively. The cap 278 is used to close the housing 210 and the bacterial suspension is mixed with the microspheres (cell concentration agent 230) at room temperature and allowed to settle into the passageway 216. The cap 278 is removed and the plunger 250 is inserted to transfer a portion of the liquid sample containing the settled microspheres and hydrogel beads into the lower receptacle 224, which contains the ATP detection reagents. The unitary device is immediately inserted into the reading chamber of a luminometer (for example, a NG Luminometer, UNG2) and RLU measurements are recorded at 10 sec interval using the Unplanned Testing mode of the UNG2 luminometer. RLU measurements are collected until the number of RLUs reaches a plateau. The data are downloaded using the software provided with the NG luminometer. The data will indicate that the microbial cells are concentrated by the microspheres, the cell extractant is released by the hydrogel, the cell extractant causes the release of ATP from the cells, and the ATP released from the cells is detected by the ATP detection system.

Example 4

Detection of Microbial Cells in a Unitary Sample Preparation and Detection Device Using an ATP Bioluminescence Detection System A unitary sample preparation and detection device 300, as shown in FIG. 3, is used in this Example. The valve actuator 372 is positioned such that the valve cavity 374 is in fluid communication with the upper receptacle 320 prior to use. The device contains approximately 10 mg of autoclaved CM-111 3M Cosmetic Microspheres in the upper receptacle 320. Lower receptacle 324 contains a liquid detection reagent 365, which consists of approximately 0.6 milliliters of the luciferase/luciferin liquid reagent solution from a Clean-Trace surface ATP system. BARDAC 205M beads are made according to Preparative Example 5 of International Publication No. WO2010/039627. Ten milliliters of sterile deionized water is added to the upper receptacle 320 of the unitary devices 300 immediately before use.

*E. coli* overnight cultures are prepared as described in Example 2. The bacterial culture is diluted to approximately $10^6$ or $10^5$ CFU/ml in Butterfield's buffer. One hundred microliters of the diluted suspension are pipetted directly into upper receptacle 320 of the unitary devices 300 to obtain a suspension of approximately $10^5$ CFU or $10^4$ CFU in ten milliliters, respectively. The cap 378 is used to close the housing 310 and the bacterial suspension is mixed with the microspheres (cell concentration agent 330) at room temperature and allowed to settle into the valve cavity 374. The cap 378 is removed and two BARDAC 205M beads (hydrogel 362) are dropped into the housing 310. Immediately after the beads settle into the valve cavity 374, the valve actuator 372 is turned to transfer the portion of the liquid sample in the valve cavity (containing the cell concentration agent 330 and the hydrogel 362) into the lower receptacle 324 containing the ATP detection reagents. The unitary device is immediately inserted into the reading chamber of a luminometer (for example, a NG Luminometer, UNG2) and RLU measurements are recorded at 10 sec interval using the Unplanned Testing mode of the UNG2 luminometer. RLU measurements are collected until the number of RLUs reaches a plateau. The data are downloaded using the software provided with the NG luminometer. The data will indicate that the microbial cells are concentrated by the microspheres, the cell extractant is released by the hydrogel, the cell extractant causes the release of ATP from the cells, and the ATP released from the cells is detected by the ATP detection system.

Example 5

Preparation of Detection Devices

Type I Devices:

For these detection devices, housings similar to the housing of FIG. 10A were constructed with the differences noted below. Reference numbers below refer to the corresponding parts in FIG. 10A. The upper parts 1012 and lower parts 1014 of the housing 1100 were obtained using the analogous components from 3M Clean-Trace™ surface ATP tests (obtained from 3M Company, Bridgend, UK). A collector 1067 with a frangible seal 1068 coupled thereto was press-fit into the upper portion of the lower part 1014; with the frangible seal 1068 facing the lower part 1014 of the housing 1100. The upper part 1012 was coupled to the lower part 1014 using a 2 cm section of 3:1 polyolefin dual wall adhesive lined heat shrink film obtained from buyheatshrink.com (part #_HSC3A-050-cc, 1.5 cm in diameter) using a heat gun (Master Appliances Corp, Racine, Wis.).

For these detection devices, plungers similar to the plunger of FIG. 2A were constructed. Reference numbers below refer to the corresponding parts in FIG. 2A. The plunger (250) was assembled using a portion of the polyolefin plastic handle (252) from a 3M Clean-Trace™ surface ATP test, a brass metal shaft (251) and an acetal piercing member 259. The handle 252 and piercing member 259 were attached to the ends of the brass shaft via threaded connections. The brass metal shaft was 11.5 cm long and 3.9 mm in diameter. A 6 mm, 6-23 thread was produced on each end of the shaft using a lathe. The piercing member 259 was fabricated from ½-inch (12.7 mm) acetal copolymer rod (part number 8497K211, obtained from McMASTER-CARR, Santa Fe Springs, Calif.) using a 10" Southbend lathe. An O ring (Buna N AS568A Dash Number 010 obtained from McMASTER-CARR) was used as the lower seal 256 and was attached to the plunger 250 approximately 11.5 mm above the piercing end 259. The plunger was surface-sterilized before each use.

Type II Devices:

These detection devices were assembled using a plunger similar to that shown and described in FIG. 5A with a tip similar to that shown in FIG. 6A. The housing was constructed as described for the Type I devices. The tip of the plunger was fabricated from ½-inch (12.7 mm) acetal copolymer rod (part number 8497K211, obtained from McMASTER-CARR, Santa Fe Springs, Calif.) using a 10" Southbend lathe. The duckbill one-way valve and a plastic retaining washer were press-fit into the recessed opening of the body of the tip of the plunger. The filter was made by machining a POREX filter (part number X6854 from Porex Corporation, Fairburn, Ga.) to the shape shown in FIG. 6A and dimensioning one end to press-fit into the recessed opening of the tip and hold the valve and retaining washer in place. The plunger was surface-sterilized before each use.

Type III Devices:

Detection devices similar to those shown in FIG. 10A were constructed with the differences noted below. Reference numbers below refer to the corresponding parts in FIG. 10A. The upper parts 1012 and lower parts 1014 of the housing 1100 were obtained using the analogous components from 3M Clean-Trace™ surface ATP tests (obtained from 3M Company, Bridgend, UK). A collector 1067 with a frangible seal 1068 coupled thereto was press-fit into the upper portion of the lower part 514; with the frangible seal 1068 facing the lower part 1014 of the housing 1100. The upper part 1012 was coupled to the lower part 1014 using a 2 cm section of 3:1 polyolefin dual wall adhesive lined heat shrink film obtained from buyheatshrink.com (part #_HSC3A-050-cc, 1.5 cm in diameter) using a heat gun (Master Appliances Corp, Racine, Wis.).

The plunger (1050) was assembled using a portion of the polyolefin plastic handle (1052) from a 3M Clean-Trace™ surface ATP test, a brass metal shaft (1051) and tip 1090. The handle 1052 and tip 1090 were attached to the ends of the brass shaft via threaded connections. The brass metal shaft was 11.5 cm long and 3.9 mm in diameter. A 6 mm, 6-23 thread was produced on each end of the shaft using a lathe. The tip 1090 was fabricated from ½-inch (12.7 mm) acetal copolymer rod (part number 8497K211, obtained from McMASTER-CARR, Santa Fe Springs, Calif.) using a 10" Southbend lathe. An O ring 1086 was attached to the tip 1090. The tip was machined to include a retaining member 1087, as shown in FIG. 10. A scraper was constructed by die-cutting a piece of 1 mm-thick polyurethane rubber and slipping it into the retaining member 1087. The outer diameter of the scraper 1086 was dimensioned to provide a tight fit with the inside of the housing 1010. The plunger was surface-sterilized before each use.

Example 6

Capture of *E Coli* from Spiked Water with Particulate Concentration Agents Using a Type I Device An isolated colony of *E. coli* (ATCC 51813) from a Tryptic Soy Agar plate (Becton Dickinson, Sparks, Md.) was used to inoculate 5 ml Tryptic Soy Broth (Becton Dickinson, Sparks, Md.) and incubated overnight in a 37° C. incubator. The overnight culture containing approximately $10^9$ colony forming units/ml (CFU/ml) was diluted 1:10,000 (to approximately $10^5$ CFU/mL, hereinafter called "initial diluted suspension") in filter sterilized 18 megaohm water. Five hundred microliters of the diluted culture were transferred to 50 ml of filter sterilized 18 megaohm water, resulting in a final concentration of about approximately 1000/ml.

An aliquot (0.5 mL) of 100× Adsorption Buffer (pH 7.2) was added to the 50 mL diluted *E. coli* suspension (hereinafter called "spiked water sample"). The contents were mixed by manual mixing for about a minute.

An amount of 10 mg of steam sterilized CM-111 was weighed and added to Type I devices prepared as described in example 5. A 10 ml volume of the spiked water sample was added to each device and the devices were capped with surface sterilized Para film. The contents were mixed by shaking manually at room temperature (25° C.) for about 30 seconds.

After mixing, the devices were incubated for various time periods (1, 5, 10 and 20 minutes, respectively) on a Thermolyne Vari Mix™ rocking platform (Barnstead International, Iowa, 14 cycles/minute). After the incubation the tubes were set on the bench top for 10 minutes to settle the particulate concentration agent, CM-111. After settling, Para film wrapping was removed and the pre-sterilized plunger device was used to pierce the foil seal and deposit the settled CM-111 agent into the lower part of the device. The supernatant was removed by using a pipette, and the lower part of the device (which contained the cell concentration agent) was separated from the upper part of the device using a razor blade. The settled CM-111 concentration agent (in approximately 100 microliters of water) was removed from the device; diluted 1:100 in sterile water, and one-milliliter aliquots of the diluted concentration agent were plated on 3M™ Petrifilm™ Aerobic Count Plate (3M Company, St. Paul, Minn.) according to the manufacturer's instructions.

As a control, the initial diluted suspension was further diluted 1:1000 dilution in sterile water and was plated as on 3M™ Petrifilm™ Aerobic Count Plate (3M Company, St. Paul, Minn.) according to the manufacturer's instructions. The particulate materials were also plated on Petrifilm™ Aerobic Count Plate as sterility controls. The plates were incubated overnight in a 37° C. incubator (VWR Orbital Shaker Incubator, VWR, West Chester, Pa.).

All plates were analyzed by using 3M™ Petrifilm™ Plate Reader (3M Company, St. Paul, Minn.) according to the manufacturer's instructions and colony counts were obtained. The results are shown in Table 2. The results were calculated using the following formula:

Capture efficiency=(Number of colonies on concentration agent/Total Number of colonies in the spiked control)×100

TABLE 2

Concentration/capture of *E. coli* from 10 ml sample. All data represent the average of two replicate tests per experiment.

| Sample | % Control | Stdev |
|---|---|---|
| 1 min | 8 | 4 |
| 5 min | 34 | 4 |
| 10 min | 33 | 11 |
| 20 min | 80 | 10 |

Example 7

Concentration of *E Coli* Using CM-111 Using a Type III Device

An isolated *E. coli* (ATCC 51813) colony was inoculated from a streak plate into 5 ml Tryptic Soy Broth (TSB, Becton Dickinson, Sparks, Md.) and incubated at 37° C. for 18-20 hours. This overnight culture at ~$10^9$ colony forming units/ml was diluted in sterile-filtered deionized water (MilliQ, Millipore, Mass.) and spiked in 10 ml of sterile-filtered deionized water to obtain final concentration of $1\times10^3$/ml and $1\times10^4$/ml (~$1\times10^4$/ml cfus and ~$1\times10^5$/ml cfus total). The spiked water was added to the housing of a Type III device containing 10 mg pre-sterilized (121 deg C., 15 minutes) powder of CM-111 (Cosmetic Microspheres-111, 3M Company, St Paul) and 100 microliters of the 100× Adsorption Buffer (pH 7.2). The housing was sealed with surface sterilized Parafilm and placed on a rocking platform The capped devices were then incubated at room temperature (25° C.) for 5 minutes contact time on a Thermolyne Vari Mix™ rocking platform (Barnstead International, Iowa, 14 cycles/minute). The devices were then allowed to stand without shaking (to allow the particles to settle by gravity force) for 5 minutes (total elapsed time for rocking and settling=10 minutes), the Parafilm was removed and the Type II device plunger inserted into the housing and was urged toward the bottom of the housing to separate the CM-111 particles from the bulk sample. When the plunger broke the frangible seal, the CM-111 particles, suspended in about 0.1 mL of the liquid sample, was transferred to the lower receptacle of the housing. The CM-111 particles were retrieved from the lower receptacle and transferred to a 1.5 ml sterile microfuge tube. A 100 microliter volume of the BacTiter-Glo™ reagent (Promega, Madison, Wis.) was added to the pellet, mixed by vortexing for 5 seconds on a VWR Fixed Speed Vortex Mixer (3200 rpm for 5 seconds) and read on a tabletop luminometer (FB12 Single Tube Luminometer, Berthold Detection Systems USA, Oak Ridge, Tenn.). A positive control ("100% signal") was prepared by testing a 100 microliter volume from a $1\times10^5$/ml and $1\times10^6$/ml suspension of the *E. coli* cells. Results were calculated using the formula below and tabulated in Table 2 below:

ATP Signal % Capture efficiency=(RLUs on CM-111 pellet/RLUS from 100% signal)×100

RLU=Relative Luciferase Units.

TABLE 2

| Sample | ATP signal in RLUs | ATP signal Capture efficiency (%) |
|---|---|---|
| *E. coli* (1 × $10^4$ cells) control (100% signal) | 30,866 | N/A |
| *E. coli* (1 × $10^5$ cells) control (100% signal) | 176,933 | N/A |
| CM-111 pellet from ~1 × $10^3$/ml sample | 27,589 | 89 |
| CM-111 pellet from ~1 × $10^4$/ml sample | 94,840 | 54 |

N = 2, Std deviation < 10%, Data normalized to water alone (16,464 RLUs) background for *E. coli* controls and normalized to unreacted CM-111 (41,424 RLUs) background for the CM-111 pellets contacted with bacteria.

From above example it can be seen that the particulate capture agents can be used to concentrate bacteria from an aqueous sample.

Example 8

Concentration of *E. coli* using CM-111 using a Type II device

An isolated *E. coli* (ATCC 33090) colony was inoculated from a streak plate into 5 ml Tryptic Soy Broth (TSB, Becton Dickinson, Sparks, Md.) and incubated at 37° C. for 18-20 hours. This overnight culture at approximately $10^8$ colony forming units/ml was diluted in sterile-filtered deionized water (MilliQ, Millipore, Mass.) and spiked in 10 ml of sterile-filtered deionized water to obtain final concentration of $10^3$/ml (approximately $10^4$ cfus total). The spiked water was added to the device already containing 10 mg pre-sterilized (121 deg C., 15 minutes) powder of CM-111 (Cosmetic Microspheres-111, 3M Company, St Paul) and 100 microliters of the 100× Adsorption Buffer. The device was sealed with surface sterilized Parafilm and placed on a rocking platform The capped devices were then incubated at room temperature (25° C.) for 1 and 9 minutes (total elapsed=time 2 mins and 10 minutes) on a Thermolyne Vari Mix™ rocking platform (Barnstead International, Iowa, 14 cycles/minute).

After the incubation the Parafilm was removed and the plunger was inserted into the housing until it contacted the frangible seal. By inserting the plunger further, to break the frangible seal, the *E. coli* bound CM-111 was transferred to the lower receptacle of the housing along with approximately 100 microliters of the liquid sample. Control tubes containing *E. coli* without microparticles were treated similarly.

The CM-111 pellet was retrieved by cutting open the lower receptacle the particles were transferred to a 1.5 ml sterile microfuge tube. A 100 microliter volume of the BacTiter-Glo™ reagent (Promega, Madison, Wis.) was added to the pellet, mixed by vortexing for 5 seconds on a VWR Fixed Speed Vortex Mixer (3200 rpm for 5 seconds) and read on a tabletop luminometer (FB12 Single Tube Luminometer, Berthold Detection Systems USA, Oak Ridge, Tenn.). For 100% signal, a 100 microliter volume from a $10^5$/ml dilution was used. Results were calculated using the formula below and tabulated in Table 3 below:

ATP Signal % Capture efficiency=(RLUs on CM-111 pellet/RLUS from about $10^4$ total *E. coli*)×100

RLU=Relative Luciferase Units.

TABLE 3

| Sample | ATP signal in RLUs | ATP signal Capture efficiency (%) |
|---|---|---|
| *E. coli* ($10^4$ cells) control | 96,544 | N/A |
| Water sample with *E. coli* (no concentration) | 25,583 | 0 |
| CM-111 pellet with concentrated *E. coli* 2 min testing time | 56,932 | 59 |
| CM-111 pellet with concentrated *E. coli* 10 min testing time | 58,543 | 61 |

N = 2, Std deviation < 10%, Data normalized to water alone (27,938 RLUs) background for *E. coli* controls and normalized to unreacted CM-111 (30,611 RLUs) background for the CM-111 pellets contacted with bacteria.

Example 9

Concentration of *E Coli* Using AB-CM-111 Using a Type II Device

A 10 mg aliquot of AB-CM (Adsorption buffer treated CM-111) was also tested for concentration of *E. coli* from 10 ml water using the procedure described in Example 8. The contact time was 9 minutes, 1 min to settle AB-CM using the POREX plunger. The data is tabulated in Table 4.

TABLE 4

| Sample | ATP signal in RLUs | ATP signal Capture efficiency (%) |
|---|---|---|
| *E. coli* ($10^4$) control | 82,845 | N/A |
| Water sample with *E. coli* (no concentration) | 733 | 1 |
| AB-CM pellet with concentrated *E. coli* | 44,105 | 53 |

N = 2, Std deviation < 10%, Data normalized to water alone (20,281 RLUs) background for *E. coli* controls and normalized to unreacted AB-CM (44,488 RLUs) background for the CM-111 pellets contacted with bacteria.

From above example it can be seen that the particulate capture agents can be used to concentrate bacteria from an aqueous sample.

Example 10

Comparative Example

Detection of *E. Coli* in Unconcentrated Samples

State-of-the-art water testing comprises a method where 100 microliters of water is tested for ATP using a standard ATP bioluminescence assay (for example, 3M CLEANT-RACE Water—Free ATP Cat. No. AQF100, available from 3M Company, St. Paul, Minn.).

An overnight culture of *E. coli* (ATCC 33090) in tryptic soy broth was diluted in sterile water to produce two suspensions. Suspension A contained approximately $10^3$ CFU/ml and Suspension B contained about $10^5$ CFU/ml.

One hundred microliter aliquots of each suspension were mixed with 100 microliter volumes of the BacTiter-Glo™ reagent (Promega, Madison, Wis.) and the resulting bioluminescence was measured with a luminometer as described in Example 8. The results are presented in Table 5.

TABLE 5

| Sample | ATP signal in RLUs | ATP signal Capture efficiency (%) after normalizing to water |
|---|---|---|
| *E. coli* ($10^4$) control (100% Signal) | 18,143 | N/A |
| Water sample (no *E. coli*) | 1,109 | N/A |
| Water sample with *E. coli* (no concentration) | 1,776 | 4% |

N = 2, Std deviation < 10%

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A unitary sample preparation and detection device, comprising:
   a housing comprising at least two receptacles with a passageway therebetween; wherein an upper receptacle of said at least two receptacles comprises an opening configured to receive a sample and contains a cell concentration agent disposed therein; wherein a lower receptacle of said at least two receptacles includes a detection reagent disposed therein and a hydrogel comprising a cell extractant;
   means for isolating the upper receptacle from the lower receptacle; and
   means for transferring the cell concentration agent from the upper receptacle to the lower receptacle.

2. The device of claim 1, wherein the cell concentration agent comprises a particulate or dispersed cell concentration agent.

3. The device of claim 1, wherein the means for isolating the upper receptacle and the lower receptacle includes a plunger, a valve, or a frangible seal.

4. The device of claim 1, wherein the means for transferring the cell concentration agent from the upper receptacle to the lower receptacle includes a plunger, a swab, or a valve.

5. The device of claim 1, wherein the device comprises a tapered inner wall.

6. The device of claim 1, wherein the hydrogel is a hydrogel bead, a hydrogel fiber, a hydrogel ribbon or a hydrogel sheet.

7. The device of claim 1, wherein the hydrogel is coated on a solid substrate.

8. The device of claim 1, wherein said at least two receptacles further comprises a third receptacle.

9. The device of claim 8, wherein the hydrogel is also disposed within the third receptacle.

10. The device of claim 1, further comprising a somatic cell extractant.

11. The device of claim 1, further comprising a plunger.

12. The device of claim 11, wherein the plunger comprises a fluid pathway.

13. The device of claim 12, wherein the fluid pathway comprises a filter.

14. The device of claim 11, wherein the plunger further comprises a scraper.

15. A kit comprising the device of claim 1.

16. The kit of claim 15, further comprising a hydrogel comprising a microbial cell extractant.

17. The kit of claim 15, further comprising a somatic cell extractant.

18. The kit of claim 15, further comprising a sample acquisition device.

19. The kit of claim 15, further comprising a plunger.

* * * * *